US010653379B2

(12) United States Patent
Rapoport et al.

(10) Patent No.: US 10,653,379 B2
(45) Date of Patent: May 19, 2020

(54) DEVICE AND METHOD FOR SPATIOTEMPORAL RECONSTRUCTION OF A MOVING VASCULAR PULSE WAVE IN THE BRAIN AND OTHER ORGANS

(71) Applicants: AngioWave Imaging, LLC, Concord, MA (US); William E. Butler, Boston, MA (US)

(72) Inventors: Benjamin I. Rapoport, New York, NY (US); William E. Butler, Boston, MA (US)

(*) Notice: Subject to any disclaimer, the term of this patent is extended or adjusted under 35 U.S.C. 154(b) by 0 days.

(21) Appl. No.: 16/165,060

(22) Filed: Oct. 19, 2018

(65) Prior Publication Data
US 2019/0046147 A1 Feb. 14, 2019

Related U.S. Application Data

(63) Continuation of application No. 15/200,083, filed on Jul. 1, 2016, now Pat. No. 10,123,761.
(Continued)

(51) Int. Cl.
G06K 9/00 (2006.01)
A61B 6/00 (2006.01)
G06T 7/00 (2017.01)

(52) U.S. Cl.
CPC ............ A61B 6/5217 (2013.01); A61B 6/481 (2013.01); A61B 6/504 (2013.01); G06T 7/0016 (2013.01);
(Continued)

(58) Field of Classification Search
None
See application file for complete search history.

(56) References Cited

U.S. PATENT DOCUMENTS 3,335,716 A 8/1967 Alt et al.
5,637,871 A 6/1997 Piety et al.
(Continued)

FOREIGN PATENT DOCUMENTS

CN 101406392 B 5/2011
EP 1322219 B1 5/2007

OTHER PUBLICATIONS

Medda et al., A wavelet clustering technique for the identification of functionally connected regions in the rat brain using resting state fMRI, IEEE Statistical Signal Processing Workshop (SSP), Aug. 2012, pp. 424-427.
(Continued)

Primary Examiner — Atiba O Fitzpatrick
(74) Attorney, Agent, or Firm — Edell, Shapiro & Finnan, LLC

(57) ABSTRACT

The brain appears to have organized cardiac frequency angiographic phenomena with such coherence as to qualify as vascular pulse waves. Separate arterial and venous vascular pulse waves may be resolved. This disclosure states the method of extracting a spatiotemporal reconstruction of the cardiac frequency phenomena present in an angiogram obtained at faster than cardiac frequency. A wavelet transform is applied to each of the pixel-wise time signals of the angiogram. If there is motion alias then instead a high frequency resolution wavelet transform of the overall angiographic time intensity curve is cross-correlated to high temporal resolution wavelet transforms of the pixel-wise time signals. The result is filtered for cardiac wavelet scale then pixel-wise inverse wavelet transformed. This gives a complex-valued spatiotemporal grid of cardiac frequency angiographic phenomena. It may be rendered with a brightness-hue color model or subjected to further analysis.

15 Claims, 5 Drawing Sheets

Related U.S. Application Data

(60) Provisional application No. 62/187,631, filed on Jul. 1, 2015.

(52) U.S. Cl.
CPC ............ *G06T 2207/10116* (2013.01); *G06T 2207/20064* (2013.01); *G06T 2207/30016* (2013.01); *G06T 2207/30104* (2013.01)

(56) References Cited

U.S. PATENT DOCUMENTS

| | | | |
|---|---|---|---|
| 5,963,676 | A | 10/1999 | Wu |
| 6,195,456 | B1 | 2/2001 | Balasubramanian et al. |
| 6,442,414 | B1 | 8/2002 | Watanabe |
| 6,549,801 | B1 | 4/2003 | Chen et al. |
| 6,842,638 | B1 | 1/2005 | Suri et al. |
| 6,975,753 | B2 | 12/2005 | Matsuura et al. |
| 6,985,632 | B2 | 1/2006 | Sato et al. |
| 7,020,314 | B1 | 3/2006 | Suri et al. |
| 7,035,679 | B2 | 4/2006 | Addison et al. |
| 7,201,892 | B2 | 4/2007 | Achilefu et al. |
| 7,359,062 | B2 | 4/2008 | Chen et al. |
| 7,602,183 | B2 | 10/2009 | Lustig et al. |
| 8,244,334 | B2 | 8/2012 | Huang et al. |
| 8,306,295 | B2 | 11/2012 | Bruder et al. |
| 8,306,303 | B2 | 11/2012 | Bruder et al. |
| 8,417,048 | B2 | 4/2013 | Reboni et al. |
| 8,559,692 | B2 | 10/2013 | Reboni et al. |
| 8,605,976 | B2 | 12/2013 | Diamant et al. |
| 8,611,633 | B2 | 12/2013 | Kwon et al. |
| 8,628,751 | B2 | 1/2014 | Neumann et al. |
| 8,948,480 | B2 | 2/2015 | Liu et al. |
| 9,019,305 | B2 | 4/2015 | Baumgart et al. |
| 9,036,780 | B2 | 5/2015 | Kyriakou et al. |
| 9,165,349 | B2 | 10/2015 | Kwon et al. |
| 9,324,005 | B2 | 4/2016 | Wadhwa et al. |
| 9,345,413 | B2 | 5/2016 | Schie et al. |
| 9,357,916 | B2 | 6/2016 | Srivastava et al. |
| 9,811,901 | B2 | 11/2017 | Wu et al. |
| 9,814,384 | B2 | 11/2017 | Schmoll |
| 9,836,849 | B2 | 12/2017 | Dickrell, III et al. |
| 10,226,176 | B2 | 3/2019 | Schmoll |
| 2007/0106146 | A1 | 5/2007 | Altmann et al. |
| 2007/0106149 | A1 | 5/2007 | Mistretta |
| 2007/0185393 | A1 | 8/2007 | Zhou et al. |
| 2008/0226149 | A1 | 9/2008 | Wischmann et al. |
| 2010/0113949 | A1 | 5/2010 | Sathyanarayana |
| 2011/0142288 | A1 | 6/2011 | Diamant et al. |
| 2014/0072190 | A1 | 3/2014 | Wu et al. |
| 2014/0072228 | A1 | 3/2014 | Rubinstein et al. |
| 2014/0072229 | A1 | 3/2014 | Wadhwa et al. |
| 2015/0045684 | A1* | 2/2015 | Schie ............... A61B 5/04017 600/523 |
| 2015/0257653 | A1 | 9/2015 | Hyde et al. |
| 2016/0135775 | A1 | 5/2016 | Mistretta et al. |
| 2016/0189394 | A1 | 6/2016 | Zhang et al. |
| 2016/0220112 | A1 | 8/2016 | Schmoll |
| 2016/0267704 | A1 | 9/2016 | Mistretta et al. |
| 2016/0349346 | A1* | 12/2016 | Cheng ............... G01R 33/56509 |

OTHER PUBLICATIONS

Mizuno-Matsumoto et al., Wavelet-crosscorrelation analysis: Non-stationary analysis of neurophysiological signals, Brain Topography, 2005, vol. 17, No. 4, pp. 237-252.
Morlet et al, Wave propagation and sampling theory-part I: Complex signal and scattering in multilayered media, Geophysics, Feb. 1982, vol. 47, No. 2, pp. 203-221.
Najmi et al., The continuous wavelet transform and variable resolution time-frequency analysis, Johns Hopkins Apl Technical Digest, 1997, vol. 18, No. 1, pp. 134-140.
Schultze-Kraft et al., Exploiting the potential of three dimensional spatial wavelet analysis to explore nesting of temporal oscillations and spatial variance in simulateous EEG-fMRI data, Progress in Biophysics and Molecular Biology, Mar. 2011, vol. 105(1-2), pp. 67-79.
Serroukh, Wavelet coefficients cross-correlation analysis of times series, Electronic Journal of Applied Statistical Analysis, 2012, vol. 5, iss. 2, pp. 289-296.
Shannon, Communication in the Presence of Noise, Proceedings of the IEEE, Feb. 1998, vol. 86, iss. 2, pp. 447-457.
Hardesty et al., Safety, efficacy, and cost of intraoperative indocyanine green angiography compared to intraoperative catheter angiography in cerebral aneurysm surgery, Journal of clinical neuroscience, Apr. 2014, pp. 1-6.
Hyvarinen et al., Indocyanine green fluorescence angiography, Ada Ophthalmologica, Aug. 1980, vol. 58(4), pp. 528-538.
Aaslid et al., Noninvasive transcranial doppler ultrasound recording of flow velocity in basal cerebral arteries, J Neurosurg, 1982, vol. 57(6), pp. 769-774.
Vo et al., Vonn distribution of relative phase for statistical image modeling in complex wavelet domain, Signal Processing, 2011, vol. 91(1), pp. 114-125.
Abramovich et al., Wavelet Analysis and Its Statistical Applications, Journal of the Royal Statistical Society Series D (The Statistician), 2000, vol. 49(1), pp. 1-29.
Kim et al., Cine MR CSF flow study in hydrocephalus: what are the valuable parameters? Acta neurochirurgica Supplement, 1998, vol. 71(6), pp. 343-346.
Kulkarni et al., Endoscopic third ventriculostomy in the treatment of childhood hydrocephalus, The Journal of Pediatrics, Aug. 2009, vol. 155, No. 2, pp. 254-259.
Meairs et al., Ultrasound, microbubbles and the blood-brain barrier, Progress in Biophysics & Molecular Biology, Apr. 2007, vol. 93(1-3), pp. 354-362.
Saikali et al., A three-dimensional digital segmented and deformable brain atlas of the domestic pig, Journal of Neuroscience Methods, Sep. 2010, vol. 192(1), pp. 102-109.
Wilson, Monro-Kellie 2.0: The dynamic vascular and venous pathophysiological components of intracranial pressure, Journal of Cerebral Blood Flow & Metabolism, May 2016, vol. 36(8), pp. 1338-1350.
Bernstein et al., Handbook of MRI Pulse Sequences, Elsevier Academic Press, 2004, pp. 443-454.
Kim et al., Phase-shift between arterial flow and ICP pulse during infusion test, Acta Neurochirurgica, Feb. 3, 2015, vol. 157(4), pp. 633-638.
Kawoos et al., Advances in Intracranial Pressure Monitoring and Its Significance in Managing Traumatic Brain Injury, International Journal of Molecular Sciences, 2015, vol. 16 (12), pp. 28979-28997.
Gabor, Theory of communication. Part 2: The analysis of hearing, Journal of the Institution of Electrical Engineers—Part III: Radio and Communication Engineering, 1946, vol. 93(26), pp. 442-445.
Goriely et al., Mechanics of the brain: perspectives, challenges, and opportunities, Biomechanics and modeling in mechanobiology, Feb. 26, 2015, vol. 14(5), pp. 931-965.
Helbok et al., Intracranial Pressure and Cerebral Perfusion Pressure Monitoring in Non-TBI Patients: Special Considerations, Neurocritical Care, 2014, vol. 21(S2), pp. S85-S94 (published online, Sep. 11, 2014, 10 pages).
Balestreri et al., Intracranial hypertension: what additional information can be derived from ICP waveform after head injury?, Ada Neurochirurgica (wien), 2004, vol. 146(2), pp. 131-141.
Carrera et al., What Shapes Pulse Amplitude of Intracranial Pressure?, Journal of Neurotrauma, Feb. 2010, vol. 27(2), pp. 317-324.
Bangare et al., Reviewing Otsu's method for image thresholding, International Journal of Applied Engineering Research, 2015, vol. 10, No. 9, pp. 21777-21783.
Bhadelia et al., Analysis of cerebrospinal fluid flow waveforms with gated phase-contrast MR velocity measurements, American Journal of Neuroradiology, Feb. 1995, vol. 16(2), pp. 389-400.
Bonnefous et al., Quantification of arterial flow using digital subtraction angiography, Medical Physics, Oct. 2012, vol. 39, iss. 10, pp. 6264-6275.

(56) References Cited

OTHER PUBLICATIONS

Chang et al., Emerging techniques for evaluation of the hemodynamics of intracranial vascular pathology, The Neuroradiology Journal, Feb. 2015, vol. 28(1), pp. 19-27.
Dawkins et al., Complications of cerebral angiography: A prospective analysis of 2,924 consecutive procedures, Neuroradiology, Aug. 2007, vol. 49, iss. 9, pp. 753-759.
Torrence et al., A Practical Guide to Wavelet Analysis, Bulletin of the American Meteorological Society, Jan. 1998, vol. 79, iss. 1, pp. 61-78.
Zou et al., Increased Phase Synchronization between Intracranial Pressure and Arterial Blood Pressure during Elevated Intracranial Pressure in Dogs, Proceedings of the 2005 IEEE, Engineering in Medicine and Biology 27th Annual Conference, Shanghai, China, Sep. 1-4, 2005, pp. 315-318.
Unekawa et al., RBC velocities in single capillaries of mouse and rat brains are the same, despite 10-fold difference in body size, Brain Research, 2010, vol. 1320, pp. 69-73.
Grinsted et al., Application of the cross wavelet transform and wavelet coherence to geophysical time series, Nonlinear Processes in Geophysics, 2004, vol. 11, pp. 561-566.
Grist et al., Time-Resolved Angiography: Past, Present, and Future, Journal of Magnetic Resonance Imaging, 2012, vol. 36(6), pp. 1273-1286.
Jiang et al., Computational Fluid Dynamics Simulations of Intracranial Aneurysms at Varying Heart Rates: A "Patient-Specific" Study, Journal of Biomechanical Engineering, Sep. 2009, vol. 131(9), pp. 09100-1-09100-11.
Kachelriess et al., ECG-correlated image reconstruction from subsecond multi-slice spiral CT scans of the heart, Medical Physics, 2000, vol. 27(12), pp. 1881-1902.
Kirk et al., Phase-only complex-valued spatial filter, Journal of the Optical Society of America, Aug. 1971, vol. 61, iss. 8, pp. 1023-1028.
Latka et al., Phase dynamics in cerebral autoregulation, American journal of physiology, heart and circulatory physiology, 2005, vol. 289(5), pp. H2272-H2279.
Shpilfoygel et al., X-ray videodensitometric methods for blood flow and velocity measurement: A critical review of literature, Medical Physics, Sep. 2000, vol. 27, iss. 9, pp. 2008-2023.
Mistretta, Sub-Nyquist acquisition and constrained reconstruction in time resolved angiography, Medical Physics, 2011, vol. 38, iss. 6, pp. 2975-2985.
Peng et al., Wavelet phase synchronization analysis of cerebral blood flow autoregulation, IEEE Transactions on Biomedical Engineering, Apr. 2010, vol. 57, No. 4, pp. 960-968.
Pereira et al., A DSA-based method using contrast motion estimation for the assessment of the intra-aneurysmal flow changes induced by flow-diverter stents, American Journal of Neuroradiology, Apr. 2013, vol. 34(4), pp. 808-815.
Anonymous, Artis Zeego, Data Sheet VC21, Multi-axis for interventional imaging, Oct. 2014, 36 pages, www.siemens.com/healthcare.
Aristotle, The History of Animals, Historia animalium, 350 BCE, Book 1, Part 16, 200 pages, http://classics.mit.edu/Aristotle/history_anim.mb.txt.
Babin et al., Segmentation and length measurement of the abdominal blood vessels in 3-D MRI images, Conference Proceedings IEEE Engineering in Medicine and Biology Society, Sep. 2-6, 2009, pp. 4399-4402.
Barfett et al., Intra-vascular blood velocity and volumetric flow rate calculated from dynamic 4D CT angiography using a time of flight technique, The International Journal of Cardiovascular Imaging, Oct. 2014, vol. 30(7), pp. 1383-1392.
Bhadelia et al., Cerebrospinal fluid pulsation amplitude and its quantitative relationship to cerebral blood flow pulsations: a phase-contrast MR flow imaging study, Neuroradiology, Apr. 1997, vol. 39(4), pp. 258-264.
Long et al., Spatiotemporal wavelet analysis for functional MRI, NeuroImage, Oct. 2004, vol. 23(2), pp. 500-516.
Daubechies, The wavelet transform, time-frequency localization, and signal analysis, IEEE Transactions on Information Theory, Sep. 1990, vol. 36, iss. 5, pp. 961-1005.
Gabor, Theory of communication. Part I: The analysis of information, Journal of the Institution of Electrical Engineers—Part III: Radio and Communication Engineering, Nov. 1946, vol. 93(26), pp. 429-441.
Goupillaud et al., Cycle-octave and related transforms in seismic signal analysis, Geoexploration, Oct. 1984, vol. 23, iss. 1, pp. 85-102.
Kuroiwa et al., Development and clinical application of near-infrared surgical microscope: preliminary report, Minimally invasive neurosurgery: MIN, Dec. 2001, vol. 44(4), pp. 240-242.
Markl et al., 4D Flow MRI, Journal of Magnetic Resonance Imaging (JMRI), Oct. 2012, vol. 36, iss. 5, pp. 1015-1036.
Moser et al., On the accuracy of EPI-based phase contrast velocimetry, Magnetic Resonance Imaging, Nov. 2000, vol. 18, iss. 9, pp. 1115-1123.
Nyquist et al., Certain topics in telegraph transmission theory, Transactions of the American Institute of Electrical Engineers, Feb. 1928, vol. 47, iss. 2, pp. 617-644.
Persson et al., Hydrocephalus prevalence and outcome in a population-based cohort of children born in 1989-1998, Acta Paediatrica, Jun. 2005, vol. 94, iss. 6, pp. 726-732.
Provost et al., 3D Ultrafast ultrasound imaging in vivo, Physics in Medicine and Biology, Sep. 10, 2014, vol. 59, iss. 19, L1-L13.
Raabe et al., Prospective evaluation of surgical microscope-integrated intraoperative near-infrared indocyanine green videoangiography during aneuryism surgery, Journal of Neurosurgery, Dec. 2005, vol. 103, iss. 6, pp. 382-989.
Rao et al., Shear strain imaging using shear deformations, Med Phys., Feb. 2008, vol. 35(2), pp. 412-423.
Rasul et al., Is endoscopic third ventriculostomy superior to shunts in patients with non-communicating hydrocephalus? A systematic review and meta-analysis of the evidence, Acta Neurochirurgica, May 2013, vol. 155, iss. 5, pp. 883-889.
Rocca, Galen on the Brain, Anatomical Knowledge and Physiological Speculation in the Second Century A.D., Feb. 1, 2003, p. 223.
Sugawara et al., Arterial path length measurements required for the pulse wave velocity, Journal of Hypertension, May 2009, vol. 27, iss. 5, pp. 1102-1104.
Tomita et al., Automated method for tracking vast numbers of FITC-labeled RBCs in microvessels of rat brain in vivo using a high-speed confocal microscope system, Microcirculation, Feb. 2008, vol. 15, iss. 2, pp. 163-174.
Unser, Sampling—50 years after Shannon, Proceedings of the IEEE, Apr. 2000, vol. 88, No. 4, pp. 569-587.
Wagshul et al., The pulsating brain: A review of experimental and clinical studies of intracranial pulsatility, Fluids and Barriers of the CNS, Jan. 18, 2011, vol. 8, iss. 5, pp. 1-23.
Weaver et al., Brain mechanical property measurement using MRE with intrinsic activation, Physics in Medicine Biology, Nov. 2012, vol. 57, No. 22, pp. 7275-7287.
Zaidi et al., Indocyanine Green Angiography in the Surgical Management of Cerebral Arteriovenous Malformations: Lessons Learned in 130 Consecutive Cases, Operative Neurosurgery, Jun. 2014, vol. 10, No. 2, pp. 246-251.
Zou et al., Intracranial pressure waves: characterization of a pulsation absorber with notch filter properties using systems analysis, J. Neurosurg Pediatrics, Jul. 2008, vol. 2(1), pp. 83-94.
Henneman et al., Phase analysis of gated myocardial perfusion single-photon emission computed tomography compared with tissue doppler imaging for the assessment of left ventricular dys-synchrony, Journal of the American College of Cardiology, Apr. 2007, vol. 49 (16), pp. 1708-1714.
Kingdom et al., Sensitivity to contrast histogram differences in synthetic wavelet-textures, Vision Research, Mar. 2001, vol. 41(5), pp. 585-598.
Li et al., Cross-frequency coupling during isoflurane anaesthesia as revealed by electroencephalographic harmonic wavelet bicoherence, Neurosciences and Neuroanaesthesia, British Journal of Anaesthesia, Mar. 2013, vol. 110(3), pp. 409-419.

(56) References Cited

OTHER PUBLICATIONS

Moore, A modification of the Rayleigh test for vector data, Biometrika, Apr. 1980, vol. 67(1), pp. 175-180.

Mousavi et al., A wavelet transform based method to determine depth of anesthesia to prevent awareness during general anesthesia, Computational and Mathematical Methods in Medicine, 2014, vol. 2014, pp. 1-13.

Rakhmanov et al., A cross-correlation method for burst searches with networks of misaligned gravitational-wave detectors, Institute of Physics Publishing, Classical and Quantum Gravity, Sep. 6, 2005, vol. 22(18), pp. S1311-S1320.

Wang et al., The residual phase estimation of a seismic wavelet using a renyi divergence-based criterion, Journal of Applied Geophysics, Jul. 2014, vol. 106, pp. 96-105.

Yu, Histogram Matching Seismic Wavelet Phase Estimation, May 2012, Masters thesis, University of Houston.

Anor et al., Modeling of blood flow in arterial trees, Focus Article, WIREs Systems Biology and Medicine, Sep./Oct. 2010, vol. 2, pp. 612-623.

Hamberg et al., Quantitative high-resolution measurement of cerebrovascular physiology with slip-ring CT, AJNR Am J Neuroradiol, Apr. 1996, vol. 17(4), pp. 639-650.

Kashif et al., Model-based non-invasive estimation of intracranial pressure from cerebral blood flow velocity and arterial pressure, Science Translational Medicine, Apr. 2012, vol. 4(129): 129ra44.

Lassen et al., Tracer Kinetic Methods in Medical Physiology, 1979, Raven Press, New York.

Linninger et al., A mathematical model of blood, cerebrospinal fluid and brain dynamics, J Mathematical Biology, Dec. 2009, vol. 59(6), pp. 729-759.

Bayer et al., Two-dimensional simulations of displacement accumulation incorporating shear strain, Ultrason Imaging, Jan. 2014, vol. 36(1), pp. 55-73.

Braun et al., High-resolution mechanical imaging of the human brain by three-dimensional multifrequency magnetic resonance elastography at 7T, NeuroImage, Apr. 2014, vol. 90, pp. 308-314.

Feingold et al., Quantitative volumetric perfusion mapping of the microvasculature using contrast ultrasound, Invest Radiol, Oct. 2010, vol. 45(10), pp. 669-674.

Gauthier et al., Assessment of quantitative perfusion parameters by dynamic contrast-enhanced sonography using a deconvolution method, an in vitro and in vivo study, J Ultrasound Med, Apr. 2012, vol. 31(4), pp. 595-608.

Johnson et al., Local mechanical properties of white matter structures in the human brain, NeuroImage, Oct. 2013, vol. 79, pp. 145-152.

Ashmead, Morelet Wavelets in quantum mechanics, Quanta, Nov. 2012, vol. 1, Issue 1, pp. 58-70.

Johnstone et al., Wavelet threshold estimators for data with correlated noise, Journal of the Royal Statistical Society: Series B (Statistical Methodology), 1997, 59(2), pp. 319-351.

Khullar et al., Wavelet-based fMRI analysis: 3-d denoising, signal separation, and validation metrics, NeuroImage, Feb. 2011, vol. 54(4), pp. 2867-2884.

Abdallah, Considerations in perioperative assessment of valproic acid coagulopathy, review article, Journal of Anaesthesiology Clinical Pharmacology, Jan.-Mar. 2014, vol. 30, iss. 1, pp. 7-9.

D'Agnolo et al., Radon-Penrose transform for D-modules, Sep. 6, 1994, pp. 1-37.

Penkov, A Geometric Approach to the Linear Penrose Transform, Transactions of the American Mathematical Society, Aug. 1985, vol. 290, No. 2, pp. 555-575.

Wolfram, Statistical mechanics of cellular automata, The Amelican Physical Society, Reviews of Modern Physics, vol. 55, No. 3, Jul. 1983, pp. 601-644.

Sturm et al., New Brain Tumor Entities Emerge from Molecular Classification of CNS-PNETs, Cell, Feb. 25, 2016, vol. 164, iss. 5, pp. 1060-1072.

Liebling et al., Wavelet-based Synchronization of Nongated Confocal Microscopy Data for 4D Imaging of the Embryonic Heart, Proceedings of SPIE 5914, Wavelets XI, 2005, vol. 591409, 6 pages.

Ehrenreich et al., New developments in the understanding of cerebral vasoregulation and vasospasm: the endothelin-nitric oxide network, CME Credit, Cleveland Clinic Journal of Medicine, Mar.-Apr. 1995, vol. 62, No. 2, pp. 105-116.

Vagharshakyan et al., Light Field Reconstruction Using Shearlel Transform, Sep. 29, 2015, pp. 1-12 (Cornell University Archive, https://arxiv.org/abs/1509.08969, arXiv:1509.08969v1).

Daubechies, Orthonormal Bases of Compactly Supported Wavelets, Communications on Pure and Applied Mathematics, 1988, vol. XLI, pp. 909-996.

Mandelshtam, The Multidimensional Filter Diagonalization Method, Journal of Magnetic Resonance, 2000, vol. 144, pp. 343-356.

Insolera et al., Cortical neurogenesis in the absence of centrioles, Nat Neurosci, Nov. 2014, vol. 17, No. 11, pp. 1528-1536.

Kool et al., Molecular subgroups of medulloblastoma: an international meta-analysis of transcriptome, genetic aberrations, and clinical data of WNT, SHH, Group 3, and Group 4 medulloblastomas, 2012, Acta Neuropathol, vol. 123, pp. 473-484.

Kutyniok et al., Compactly Supported Shearlets, Approximation Theory XIII: San Antonio 2010, pp. 1-24.

Liner, An overview of wavelet transform concepts and applications, University of Houston, Feb. 26, 2010, pp. 1-17.

Liu et al., Motion Magnification, ACM Transactions on Graphics (TOG), Jul. 2005, vol. 24, iss. 3, pp. 519-526 (8 pages).

Lohani et al., Intrasacral meningocele in the pediatric population, J Neurosurg Pediatrics, Jun. 2013, vol. 11, pp. 615-622.

Long et al., Spatiotemporal wavelet analysis for functional MRI, NeuroImage, 2004, vol. 23, pp. 500-516.

Maltz et al., Fixed gantry tomosynthesis system for radiation therapy image guidance based on a multiple source x-ray tube with carbon nanotube cathodes, Medical Physics, May 2009, vol. 36, No. 5, pp. 1624-1636.

Mandelshtam, FDM: the filter diagonalization method for data processing in NMR experiments, Progress in Nuclear Magnetic Resonance Spectroscopy, 2001, vol. 38, pp. 159-196.

Mourant et al., Hemoglobin parameters from diffuse reflectance data, Journal of Biomedical Optics, Mar. 2014, vol. 19, No. 3, pp. 037004-1-037004-9.

D'Ariano, How to Derive the Hilbert-Space Formulation of Quantum Mechanics From Purely Operational Axioms, 20 pages (presented at conference "On the Present Status of Quantum Mechanics" held on Sep. 7-9, 2005, Mali Losinj, Croatia) (Cornell University Archive, https://arxiv.orgLabs/quant-ph/0603011, arXiv:quant-ph/0603011v1).

Mixter, Ventriculoscopy and Puncture of the Floor of the Third Ventricle, Boston M. & S. Journal, Mar. 1, 1923, vol. 188, No. 9, pp. 277-278.

Moussa et al., Efficacy of postoperative antibiotic injection in and around ventriculoperitoneal shunt in reduction of shunt infection: A randomized controlled trial, Clinical Neurology and Neurosurgery, 2016, vol. 143, pp. 144-149.

Monici, Cell and tissue autofluorescence research and diagnostic applications, Biotechnology Annual Review, 2005, vol. 11, pp. 227-256.

Drexler et al., In vivo ultrahigh-resolution optical coherence tomography, Optics Letters, Sep. 1, 1999, vol. 24, No. 17, pp. 1221-1223.

Rees et al., Role of endothelium-derived nitric oxide in the regulation of blood pressure, Proc. Natl. Acad. Sci. USA, 1989, vol. 86, pp. 3375-3378.

Rodino et al., The Gabor Wave Front Set (2013) (Cornell University Archive, https://arxiv.org/abs/1207.5628,arXiv:1207.5628v2), pp. 1-29.

Schaer et al., Haptoglobin Preserves Vascular Nitric Oxide Signaling during Hemolysis, American Journal of Respiratory and Critical Care Medicine, May 15, 2016, vol. 193, iss. 10, pp. 1111-1122.

Shumacher, Analog clock and watch reader, 2015, pp. 1-10 (https://www.cs.bgu.ac.il/~ben-shahar/Teaching/Computational-Vision/StudentProjects/ICBV151/ICBV-2015-1-ChemiShumacher/Report.pdf).

(56) References Cited

OTHER PUBLICATIONS

Tudor et al., Endoscopic third ventriculostomy (ETV) for idiopathic normal pressure hydrocephalus (iNPH) (Review), Cochran Collection, Cochrane Database of Systematic Reviews, 2015, iss. 7, pp. 1-23.
Khandelwal et al., Age-dependent increase in green autofluorescence of blood erythrocytes, J. Biosci. Sep. 2007, vol. 32, No. 6, pp. 1139-1145.
Szathmary et al., The major evolutionary transitions, Mar. 16, 1995, Nature, vol. 374, pp. 227-232.
Wadhwa et al., Phase-Based Video Motion Processing, MIT Computer Science and Artificial Intelligence Lab, ACM Transactions on Graphics, Jul. 2013, vol. 32, No. 4, article 80, pp. 80:1-80:9.
Yang et al., Improved phase-resolved optical Doppler tomography using the Kasai velocity estimator and histogram segmentation, Optics Communications, Jul. 15, 2002, vol. 208, pp. 209-214.
Zhang et al., Orthogonal Complex Filter Banks and Wavelets: Some Properties and Design, IEEE Transactions on Signal Processing, Apr. 1999, vol. 47, No. 4, pp. 1039-1048.
Aaslid et al., Cerebral Autoregulation Dynamics in Humans, Stroke, 1989, vol. 20, pp. 45-52.
Adams et al., Symptomatic Occult Hydrocephalus with "Normal" Cerebrospinal-Fluid Pressure, A Treatable Syndrome, The New England Journal of Medicine, Jul. 15, 1965, vol. 273, No. 3, pp. 117-126.
Barina, Gabor Wavelets in Image Processing, Feb. 10, 2016, 6 pages (Cornell University Archive, https://arxiv.org/pdf/1602.03308.pdf, arXiv:1602.03308v1).
Bernardes et al., Digital Ocular Fundus Imaging: A Review, Ophthalmologica, 2011, vol. 226, pp. 161-181.
Bernardino et al., A Real-Time Gabor Primal Sketch for Visual Attention, Second Iberian Conference on Pattern Recognition and Image Analysis, 2005, 8 pages (http://vislab.isr.ist.utl.pt/publications/05-ibpria-alex.pdf).
Guo et al., Wavelets with composite dilations and their MRA properties, Applied and Computational Harmonic Analysis, 2006, vol. 20, pp. 202-236.
Goh et al., Subependymal giant cell tumors in tuberous sclerosis complex, Neurology, Oct. 2004, vol. 63, pp. 1457-1461.
Bo et al., Symbolic Representations in Motor Sequence Learning, Neuroimage, 2011, vol. 54, No. 1, pp. 417-426.
Bodranghien et al., Consensus Paper: Revisiting the Symptoms and Signs of Cerebellar Syndrome, Cerebellum, Jun. 2016, vol. 15, No. 3, pp. 369-391 (published online Jun. 2015) (23 pages).
Borsdorf et al., Separate CT-Reconstructions for 3D Wavelet Based Noise Reduction Using Correlation Analysis, 2007, IEEE Nuclear Science Symposium Conference Record, pp. 2633-2638.
Brouder et al., A Smooth Introduction to the Wavefront Set, Apr. 7, 2014, pp. 1-29 (Cornell University Archive, https://arxiv.org/pdf/1404.1778.pdf, arXiv:1404.1778v1).
Burt et al., The Laplacian Pyramid as a Compact Image Code, IEEE Transactions on Communications, Apr. 1983, vol. COM-31, No. 4, pp. 532-540.
Zhao et al., Ultrasound Contrast Imaging Based on a Novel Algorithm Combined Pulse Inversion with Wavelet Transform, Ultrasound in Medicine & Biology, 2011, vol. 37, No. 8, pp. 1292-1305.
Faubel et al., Cilia-based flow network in the brain ventricles, Neurophysiology, Jul. 8, 2016, vol. 353, iss. 6295, pp. 176-178.
Marshall et al., Cilia orientation and the fluid mechanics of development, Current Opinion in Cell Biology, 2008, vol. 20(1), pp. 48-52.
Ohata et al., Mechanosensory Genes Pkd1 and Pkd2 Contribute to the Planar Polarization of Brain Ventricular Epithelium, The Journal of Neuroscience, Aug. 5, 2015, vol. 35(31), pp. 11153-11168.
Jalalvand et al., Ciliated neurons lining the central canal sense both fluid movement and pH through ASIC3, Nature Communications, Jan. 8, 2016, pp. 1-12.
Wagshul et al., Resonant and notch behavior in intracranial pressure dynamics, J Neurosurgery Pediatrics, May 2009, vol. 3(5), pp. 354-364.
Park et al., Alterations of pulsation absorber characteristics in experimental hydrocephalus, J Neurosurg Pediatrics, Aug. 2010, vol. 6(2), pp. 159-170.
Kotelnikov, On the transmission capacity of the "ether" and of cables in electrical communication, Proceedings of the first All-Union Conference on the technological reconstruction of the communications sector and low-current engineering, Moscow 1933, vol. 1, pp. 1-23.
Sagel et al., Gated computed tomography of the human heart, Investigative radiology, Nov.-Dec. 1977, vol. 12, iss. 6, pp. 563-566.
Sarode et al., Video Motion Magnification Using Spatio-Temporal Algorithm, International Journal of Computer Applications (0975-8887), Jun. 2014, vol. 96, No. 9, pp. 9-13.
Zhao et al., Phase-Resolved Optical Coherence Tomography and Optical Doppler Tomography for Imaging Blood Flow in Human Skin with Fast Scanning Speed and High Velocity Sensitivity, Optics Letters, Jan. 15, 2000, vol. 25, iss. 2, pp. 114-116.
Wu et al., Eulerian Video Magnification for Revealing Subtle Changes in the World, ACM Transactions on Graphics, Jul. 1, 2012, vol. 31, iss. 4, pp. 1-8.
Wang et al., Phase-Sensitive Optical Coherence Elastography for Mapping Tissue Microstains in Real Time, Applied Physics Letter, 2007, vol. 90, pp. 164105-1-164105-3.
Robles et al., Assessing Hempglobin Concentration Using Spectroscopic Optical Coherence Tomography for Feasibility of Tissue Diagnostics, Biomedical Optics Express, Aug. 2, 2010, vol. 1, No. 1, pp. 310-317.
Lahiri et al., Medical Applications of Infrared Thermography: A Review, Infrared Physics & Technology, 2012, vol. 55, pp. 221-235.
Mourant et al., Hemoglobin Parameters from Diffuse Reflectance Data, Journal of Biomedical Optics, Mar. 2014, vol. 19, iss. 3, pp. 037004-1-037004-9.
Makita et al., Optical Coherence Angiography, Optics Express, Aug. 21, 2006, vol. 14, No. 17, pp. 7821-7840.
Chen et al., Noninvasive Imaging of in vivo blood flow velocity using optical Doppler tomography, Optics Letters, Jul. 15, 1997, vol. 22, No. 14, pp. 1119-1121.
Izatt et al., In vivo bidirectional color Doppler flow imaging of picoliter blood vols. using optical coherence tomography, Optics Letters, Sep. 15, 1997, vol. 22, No. 18, pp. 1439-1441.
Drexler, Ultrahigh-Resolution Optical Coherence Tomography, Journal of Biomedical Optics, Jan./Feb. 2004, vol. 9, iss. 1, pp. 47-74.
Devor et al., Frontiers in optical imaging of cerebral blood flow and metabolism, Journal of Cerebral Blood Flow & Metabolism, 2012, vol. 32, pp. 1259-1276.
Chen et al., Optical Doppler Tomography, IEEE Journal on Selected Topics in Quantum Electronics, Jul. 1, 1999, vol. 5, No. 4, pp. 1134-1142.
Bachmann et al., Fluorescence Spectroscopy of Biological Tissues—A Review, Applied Spectroscopy Reviews, 2006, vol. 41, pp. 575-590.
Desmettre et al., Fluorescence Properties and Metabolic Features of Indocyanine Green (ICG) as Related to Angiography, Survey of Ophthalmology, Jul.-Aug. 2000, vol. 45, No. 1, pp. 15-27.
Martin et al., Hydrodynamic and longitudinal impedance analysis of cerebrospinal fluid dynamics at the craniovertebral junction in type I Chiari malformation, PLoS One, Oct. 2013, vol. 8, iss. 10, pp. 1-9.
Tuy, An Inversion Formula for Cone-Beam Reconstruction, Society for Industrial and Applied Mathematics, Jun. 1983, vol. 43, No. 3, pp. 546-552.
Candes et al., New Tight Frames of Curvelets and Optimal Representations of Objects with C2 Singularities, Nov. 2002, pp. 1-39 (http://citeseerxist.psu.edu/viewdoc/download?doi=10.1.1.162.1548&rep=rep1&type=pdf).
Cense et al., Ultrahigh-resolution high-speed retinal imaging using spectral-domain optical coherence tomography, Optics Express, May 31, 2004, vol. 12, No. 11, pp. 2435-2447 (13 pages).
Cheng et al., Mammalian DNA Methyltransferases: A Structural Perspective, Structure, Review, Mar. 2008, vol. 16, No. 3, pp. 341-350.

(56) References Cited

OTHER PUBLICATIONS

Coumans et al., Volumetric analysis of syringomyelia following hindbrain decompression for Chiari malformation Type I: syringomyelia resolution follows exponential kinetics, Neurosurg Focus, Sep. 2011, vol. 31, No. 3:E4, pp. 1-4.
Deutsch et al., Information Flow in Entangled Quantum Systems, (1999) pp. 1-24 (https://arxiv.org/ftp/quant-ph/papers/9906/9906007.pdf).
Donoho, Compressed Sensing, Sep. 14, 2004, pp. 1-34.
Donoho et al., Message-Passing Algorithms for Compressed Sensing, PNAS, Nov. 10, 2009, vol. 106, No. 45, pp. 18914-18919.
Duverger et al., Concentrations of Putative Neurovascular Transmitters in Major Cerebral Arteries and Small Pial Vessels of Various Species, Journal of Cerebral Blood Flow and Metabolism, 1987, vol. 7, No. 4, pp. 497-501.
Eastwood, The Penrose Transform for Complex Projective Space, Cornell University Archive, Aug. 17, 2008, pp. 1-11 (https://arxiv.org/abs/0808.2321, arXiv:0808.2321v1).
Eastwood et al., Cohomology and Massless Fields, Commun. Math. Phys. (1981) vol. 78, pp. 305-351.
Edelman et al., Nitric Oxide: Linking Space and Time in the Brain, Proc. Natl. Acad. Sci. USA, Dec. 1992, vol. 39, pp. 11651-11652.
Feichtinger et al., Gabor Frames and Time-Frequency Analysis of Distributions, Journal of Functional Analysis, 1997, vol. 146, No. FU963078, pp. 464-495.
Feng et al., Conservation and Divergence of Methylation Patterning in Plants and Animals, PNAS, May 11, 2010, vol. 107, No. 19, pp. 8689-8694.
Fisher et al., Group Formation, Relatedness, and the Evolution of Multicellularity, Current Biology, Jun. 17, 2013, vol. 23, No. 12, pp. 1120-1125.
Fujimoto et al., Optical Coherence Tomography: An Emerging Technology for Biomedical Imaging and Optical Biopsy, Neoplasia, Jan.-Apr. 2000, vol. 2, Nos. 1-2, pp. 9-25.
Goriely et al., Mechanics of the brain: perspectives, challenges, and opportunities, Biomech Model Mechanobiol, 2015, vol. 14, pp. 931-965.
Guerquin-Kern et al., A Fast Wavelet-Based Reconstruction Method for Magnetic Resonance Imaging, IEEE Transactions on Medical Imaging, Institute of Electrical and Electronics Engineers, 2011, 14 pages (obtained from HAL archives-ouvertes).
Guo et al., Sparse Multidimensional Representations using Anisotropic Dilation and Shear Operators, 2005, 13 pages (https://www.math.uh.edu/~dlabate/Athens.pdf).
Han, Properties of Discrete Framelet Transforms, Math. Model. Nat. Phenom., 2013, vol. 8, No. 1, pp. 18-47 (32 pages).
Heil, What is a Frame?, Notices of the AMS, 2013, vol. 60, No. 6, pp. 748-750.
Herz et al., Ultrahigh resolution optical biopsy with endoscopic optical coherence tomography, Optics Express, Jul. 26, 2004, vol. 12, No. 15, pp. 3532-3542.
Hogeweg, Cellular Automata as a Paradigm for Ecological Modeling, Applied Mathematics and Computation, 1988, vol. 27, pp. 81-100.
Hormander, The Spectral Function of an Elliptic Operator, Ada Math, May 7, 1968, vol. 121, pp. 193-218.
Huff et al., Dnmt1-Independent CG Methylation Contributes to Nucleosome Positioning in Diverse Eukaryotes, Cell, Mar. 13, 2014, vol. 156, No. 6, pp. 1286-1297.
Januszewski et al., Flow-based evalution of cerebral revascularization using near-infrared indocyanine green videoangiography, Neurosurg Focus, Feb. 2014, vol. 36, No. 2: E14, pp. 1-8.
Jia et al., Quantitative OCT angiography of optic nerve head blood flow, Biomedical Optics Express, Dec. 1, 2012, vol. 3, No. 12, pp. 3127-3137.
Kamble et al., A Review: Eulerian Video Motion Magnification, International Journal of Innovative Research in Computer and Communication Engineering, Mar. 2015, vol. 3, iss. 3, pp. 2384-2390.
Kim et al., Epigenetic mechanisms in mammals, Cellular and Molecular Life Sciences, 2009, vol. 66, pp. 596-612.
Kittipoom et al., Construction of Compactly Supported Shearlet Frames, Cornell University Archive, 2010, pp. 1-37 (https://arxiv.org/abs/1003.5481, arXiv:1003.5481v2).
Klimenko et al., A cross-correlation technique in wavelet domain for detection of stochastic gravitational waves, 2002, pp. 1-15 (https://arxiv.org/abs/gr-qc/0208007, arXiv:gr-qc/0208007v1).
Knopfmacher et al., Graphs, partitions and Fibonacci numbers, Discrete Applied Mathematics, 2007, vol. 155, pp. 1175-1187.
Koenig et al., Regression of Subependymal Giant Cell Astrocytoma With Rapamycin in Tuberous Sclerosis Complex, J Child Neurol., Oct. 2008, vol. 23, No. 10, pp. 1238-1239.
Koonin, The Biological Big Bang model for the major transitions in evolution, Biology Direct, Aug. 20, 2007, vol. 2, No. 21, pp. 1-17.
Kramer et al., Intraventricular fibrinolysis with tissue plasminogen activator is associated with transient cerebrospinal fluid inflammation: a randomized controlled trial, Journal of Cerebral Blood Flow & Metabolism, 2015, vol. 35, pp. 1241-1248.
Kutyniok et al., Resolution of the Wavefront Set using Continuous Shearlets, Transactions of the American Mathematical Society, May 2009, vol. 361, No. 5, pp. 2719-2754.
Kutyniok et al., Image Separation using Wavelets and Shearlets, International Conference on Curves and Surfaces, 2010, pp. 1-14 (https://www.math.tu-berlin.de/fileadmin/i26_fg-kutyniok/Kutyniok/Papers/ImageSeparation.pdf).
Lee, Wavelet-Vaguelette Decompositions and Homogeneous Equations, Dec. 1997, Purdue University, In Partial Fulfillment of the Requirements for the Degree of Doctor of Philosophy, 103 pages.
Lindenmayer, Developmental Algorithms for Multicellular Organisms: A Survey of L-Systems, J. Theor. Biol., 1975, vol. 54, pp. 3-22.
Lopez et al., The Cauchy problem for a forced harmonic oscillator, Revista Mexicana De Fisica, Dec. 2009, vol. 35, No. 2, pp. 196-215.
Luney et al., Acute Posterior Cranial Fossa Hemorrhage—Is Surgical Decompression Better than Expectant Medical Management?, Neurocritical Care, Apr. 12, 2016, 6 pages.
Gabor, Theory of Communication, Part 3: Frequency Compression and Expansion, 1946, vol. 93, No. 26, pp. 445-457.
Havla et al., Wavelet-based calculation of cerebral angiographic data from time-resolved CT perfusion acquisitions, Eur Radiol. Aug. 2015, vol. 25, No. 8, pp. 2354-2361 (published online Feb. 26, 2015) (8 pages).
Kamp et al., Microscope-Integrated Quantitative Analysis of Intraoperative Indocyanine Green Fluorescence Angiography for Blood Flow Assessment: First Experience in 30 Patients, Operative Neurosurgery 1, vol. 70, Mar. 2012, pp. ons65-ons74.
Mazzola et al., Pediatric Hydrocephalus: systematic literature review and evidence-based guidelines. Part 2: Management of posthemorrhagic hydrocephalus in premature infants, Nov. 2014, J Neurosurg Pediatrics (Suppl), vol. 14, pp. 8-23.
McCrory et al., Consensus statement on concussion in sport: the 4th International Conference on Concussion in Sport held in Zürich, Nov. 2012, Br J Sports Med, (2013), vol. 47, pp. 250-258.
Michod et al., Cooperation and Conflict in the Evolution of Multicellularity, 2001, The Genetics Society of Great Britain, Heredity, vol. 86, pp. 1-7.
Nehra et al., Peyronie's Disease: AUA Guideline, American Urological Association (AUA) Guideline, approved Apr. 2015, pp. 1-41.
Zhang et al., "Application of Wavelet Thresholding De-noising in DSA," International Symposium on Information Science and Engineering IEEE Computer Society, 2008, pp. 130-134.
Akram et al., "Blood Vessel Enhancement and Segmentation Using Wavelet Transform, International Conference on Digital Image Processing IEEE Computer Society," 2009, pp. 34-38.
Cao et al., "Joint Spatio-Temporal Registration and Microvasculature Segmentation of Retinal Angiogram Sequences," 33rd Annual International Conference of the IEEE EMBS, 2011, pp. 2618-2621.
Tsai et al., "Motion Estimation and Wavelet Transform in Angiogram Video Coding," IEEE, 1994, pp. 1121-1125.

(56) References Cited

OTHER PUBLICATIONS

Oh et al., "Reversible Wavelet Compression for Digital Angiograms," Proceedings of the 20th Annual International Conference of the IEEE Engineering in Medicine and Biology Society,1998, vol. 20, No. 3, pp. 1442-1445.
Tache et al., "Enhanced Visualization of Cerebral Blood Vessels for X-ray Angiograms," IEEE International Conference on E-Health and Bioengineering, 2013, pp. 1-13.
Sun et al., "Morphological enhancement of vascular angiogram with multiscale detected by Gabor filters," Electronics Letters, 2008, vol. 44, No. 2, pp. 1-3.
Munteanu et al., "Wavelet-Based Lossless Compression of Coronary Angiographic Images," IEEE Transactions on Medical Imaging, 1999, vol. 18, No. 3, pp. 272-281.
Lin et al., "Extraction of Coronary Arterial Tree Using Cine X-Ray Angiograms," Biomedical Engineering-Applications, Basis & Communications, 2005, pp. 111-120.
Hohne et al., "Fourier Domain Techniques for Digital Angiography of the Heart," IEEE Transactions on Medical Imaging, 1984, vol. MI-3, No. 2, pp. 62-67.
Hohne et al., "Proceedings of SPIE: Digital Angiography of the Heart in the Frequency Domain," Medical Images and Icons IEEE, 1984, pp. 245-250.
Havla et al., "Validation of a method to differentiate arterial and venous vessels in CT perfusion data using linear combinations of quantitative time-density curve characteristics," Eur. Radiol., 2015, vol. 25, pp. 2937-2944.
Farge, M., "Wavelet Transforms and Their Applications to Turbulence," Annu. Rev. Fluid Mech., 1992, vol. 24, pp. 395-457.
Havla, et al., "Classification of arterial and venous cerebral vasculature based on wavelet postprocessing of CT perfusion data," Med. Phys. (2016) 43 (2), pp. 702-709.
Forbes et al., Statistical Distributions, Fourth Edition, copyright 2011, John Wiley and Sons, Inc., Chapters 1-9, (84 pages).
Bracewell, Two-Dimensional Imaging, copyright 1995, Prentice Hall, chapters 4-7, 12, and 15 (206 pages).
Mandelshtam et al., Harmonic inversion of time signals and its applications, AIP the Journal of Chemical Physics 1997, vol. 107, No. 6756, 12 pages (Abstract).
Schroeder, The Simple Harmonic Oscillator, copyright 2015-2016, 5 pages (https://physics.weber.edu/schroeder/quantum/Harmonic.pdf).
International Standards Organization, ISO/IEC 14496-12 Multimedia Formats Information Technology—Coding of audio-visual objects (2008) 4 pages (Abstract).
Des Plantes, Eine Neue Methode Zur Differenzierung in der Rontgenographie (Planigraphies), Acta Radiologica, (1932)132, 182-192 (DOI: 10.3109/00016923209135135) (English abstract).
Guido et al., Introduction to the special issue on wavelet-based algorithms for medical problems (2007) vol. 37, p. 429.
Nielsen, Conditions for a Class of Entanglement Transformations, Aug. 17, 1999, pp. 1-4 (Cornell University Archive, arXiv No. quant-ph/9811053v2).
Novotny et al., A Method of Photographing Fluorescence in Circulating Blood in the Human Retina, Circulation, vol. XXIV, Jul. 1961, pp. 82-86.
Pewsey et al., Circular Statistics in R, Oxford University Press, (2013) Chapters 1-3, 7 and Appendix (80 pages).
Pfister et al., Molecular diagnostics of CNS embryonal tumors, Acta Neuropathology, Nov. 2010, vol. 120, No. 5, pp. 553-566.
Pollock, Dyadic Wavelets Analysis, (2016) pp. 1-26.
Qian et al., High Resolution Stationary Digital Breast Tomosynthesis using Distributed Carbon Nanotube X-ray Source Array, Medical Physics, (Apr. 2012) vol. 39, No. 4, pp. 2090-2099.
Rashid-Farrokhi et al., Wavelet-Based Multiresolution Local Tomography, IEEE Transactions on Image Processing, Oct. 1997, vol. 6, No. 10, pp. 1412-1430.
Rollins et al., Real-time in vivo color Doppler optical coherence tomography, Journal of Biomedical Optics, Jan. 2002, vol. 7, No. 1, pp. 123-129.
Ronneberger et al., U-Net: Convolutional Networks for Biomedical Image Segmentation, May 18, 2015, pp. 1-8 (Cornell University Archive, arXiv No. 1505.04597v1).
Ruzhansky, Introduction to pseudo-differential operators, Jan. 21, 2014, pp. 1-54.
Sadowsky, The Continuous Wavelet Transform: A Tool for Signal Investigation and Understanding, John Hopkins APL Technical Digest, 1994, vol. 15, No. 4, pp. 306-318.
Saito et al., Efficient Gene Transfer into the Embryonic Mouse Brain Using in Vivo Electroporation, Developmental Biology, 2001, vol. 240, pp. 237-246.
Sen et al., 3D ROI Image Reconstruction from Truncated Computed Tomogrpahy, IEEE Transactions on Medical Imaging, May 26, 2013, pp. 1-24.
Shen et al., Growth hormone therapy and risk of recurrence/progression in intracranial tumors: a meta-analysis, Neurol Sci, 2015, vol. 36, pp. 1859-1867.
Shy et al., X-Y separable pyramid steerable scalable kernels, (1994) pp. 237-244 (https://authors.library.caltech.edu/3438/1/SHYcvpr94.pdf).
Valens, A Really Friendly Guide to Wavelets, 1999, pp. 1-19.
Vrhel et al., Fast Computation of the Continuous Wavelet Transform through Oblique Projections, (1996) pp. 1-4 http://citeseerx.ist.psu.edu/viewdoc/download?doi=10.1.1.66.3780&rep=rep1&type=pdf).
Wang et al., Three dimensional optical angiography, Optics Express, Apr. 2, 2007, vol. 15, No. 7, pp. 4083-4097.
Wang et al., Doppler optical micro-angiography for volumetric imaging of vascular perfusion in vivo, May 25, 2009, Optics Express, vol. 17, No. 11, pp. 8926-8940.
Yang et al., The X-Ray Transform Projection of 3D Mother Wavelet Function, Research Article, Computational and Mathematical Methods in Medicine, 2013, Article ID 754829, 9 pages.
Yazdanfar et al., High resolution imaging of in vivo cardiac dynamics using color Doppler optical coherence tomography, Optics Express, Dec. 22, 1997, vol. 1, No. 13, pp. 424-431.
Zhu et al., Endothelial nitric oxide synthase: a potential therapeutic target for cerebrovascular diseases, Molecular Brain, 2016, vol. 9, No. 30, pp. 1-8.
Zhuang et al., Fan-beam and cone-beam image reconstruction via filtering the backprojection image of differentiated projection data, Institute of Physics Publishing, Physics in Medicine and Biology, 2004, vol. 49, pp. 5489-5503.
Taylor et al., Molecular subgroups of medulloblastoma: the current consensus, Consensus Paper, Acta Neuropathol, 2012, vol. 123, pp. 465-472.
Thavavel et al., Regularized Computed Tomography using Complex Wavelets, International Journal of Magnetic Resonance Imaging, 2007, vol. 01, No. 01, pp. 027-032.
Thielen et al., Ultrafast dynamic computed tomography myelography for the precise identification of high-flow cerebrospinal fluid leaks caused by spiculated spinal osteophytes, J Neurosurg Spine, Clinical Article, Mar. 2015, vol. 22, pp. 324-331.
Spaide et al., Retinal Vascular Layers Imaged by Fluorescein Angiography and Optical Coherence Tomography Angiography, Original investigation, JAMA Opthalmology, Jan. 2015, vol. 133, No. 1, pp. 45-50.
Ren et al., Phase-resolved functional optical coherence tomography: simultaneous imaging of in situ tissue structure, blood flow velocity, standard deviation, birefirngence, and Stokes vectors in human skin, Optics Letters, Oct. 1, 2002, vol. 27, No. 19, pp. 1702-1704.
Rocca, Galen on the Brain: Anatomical Knowledge and Physiological Speculation in the Second Century Ad, Studies in Ancient Medicine, 2003, vol. 26, Chapter 6 (63 pages).
Shenoi, Introduction to Digital Signal Processing and Filter Design, Wiley, 2006, Chapters 3-5 (217 pages).
Srinivasan et al., Quantitative Cerebral Blood Flow with Optical Coherence Tomography, Optics Express, Feb. 1, 2010, vol. 18, No. 3, pp. 2477-2494.
Steane, An introduction to spinors, Dec. 13, 2013, pp. 1-23 (Cornell University Archive, arXiv No. 1312.3824v1).

(56) References Cited

OTHER PUBLICATIONS

Thompson et al., Prognostic Value of Medulloblastoma Extent of Resection After Accounting for Molecular Subgroup: A Retrospective Integrated Clinical and Molecular Analysis, Lancet Oncol. Apr. 2016, vol. 17, No. 4, pp. 484-495.
Timmons, Image-Guided Neurosurgery: Integration of Medical Image Data with a Real-time View of the Surgical Field, Jun. 1997, pp. 1-66.
Tran et al., Learning Spatiotemporal Features with 3D Convolutional Networks, Proceedings of the 2015 IEEE International Conference on Computer Vision (ICCV), (2015) pp. 4489-4497.
Rao et al., Shear strain imaging using shear deformations (2008) Med. Phys. 35(2):412-423.
Weaver et al., Brain mechanical property measurement using MRE with intrinsic activation Phys. Med. Biol. (2012) 57:7275-7287.
Kashif et al., Model-Based Noninvasive Estimation of Intracranial Pressure from Cerebral Blood Flow Velocity and Arterial Pressure, Sci. Transl. Med. (2012) vol. 4, No. 129, pp. 1-10.
Bayer et al., Two-Dimensional Simulations of Displacement Accumulation Incorporating Shear Stain, Ultrason. Imaging (2014) vol. 36(1):55-73.
Feingold et al., Quantitative volumetric perfusion mapping of the microvasculature using contrast ultrasound, Invest Radiol. (2010) 45:669-674.
Johnson et al., Local mechanical properties of white matter structures in the human brain, NeuroImage (2013) 79:145-152.
Khullar et al., Wavelet-based fMRI analysis: 3-D denoising, signal seperation, and validation metrics, NeuroImage (2011) 54:2867-2884.
Lee et al., Wavelet Methods for Inverting the Radon Transform with Noisy Data, IEEE Transactions on Image Processing, (2001) vol. 10, No. 1, pp. 79-94 (16 pages) (https://www.math.purdue.edu/~lucier/692/tomography.pdf).
Kutyniok et al., ShearLab 3D: Faithful Digital Shearlet Transforms based on Compactly Supported Shearlets, (2014) (39 pages) (Cornell University Archive, arXiv No. 1402.5670v1).
R-Forge User's Manual, (2011), SVN Revision: 227, 10 pages.
Daubechies Ten Lectures of Wavelets, Springer-Verlag, (1992), from CBMS-NSF Regional Conference Series in Applied Mathematics Society for Industrial and Applied Mathematics 1990 (344 pages).
Lawton, Seven Aneurysms Tenets and Techniques for Clipping (2011) Section 1, Thieme Medical Publishers, New York, Section 1, (36 pages).

\* cited by examiner

US 10,653,379 B2

DEVICE AND METHOD FOR SPATIOTEMPORAL RECONSTRUCTION OF A MOVING VASCULAR PULSE WAVE IN THE BRAIN AND OTHER ORGANS

CROSS-REFERENCE TO RELATED APPLICATIONS

The present application is a continuation of, and claims priority to, U.S. application Ser. No. 15/200,083, filed Jul. 1, 2016, which is hereby incorporated by reference in its entirety. The present application further claims the benefit of U.S. Provisional Application No. 62/187,631, filed Jul. 1, 2015, which is hereby incorporated by reference in its entirety.

FIELD OF THE DISCLOSURE

The disclosure is directed to a method for spatiotemporal reconstruction of a moving vascular pulse wave in the brain and other organs. The disclosure is further directed to a device for spatiotemporal reconstruction of a moving vascular pulse wave in the brain and other organs. This disclosure is motivated by the desire to reconstruct the motions of vascular pulse waves in the brain. The same methods can apply to any organ with a blood supply.

BACKGROUND OF THE INVENTION

The heart sends blood to the brain as a sequence of stroke volumes. Yet the equivalent volume of blood that moves to the brain with each heart beat has a measurable mortality if freely released into the cranial cavity. This implies that the brain has a set of adaptations that enables it to handle the volume and kinetic energy load attached to each heartbeat of blood that enters the brain. The ventricles of the brain, which hold spinal fluid, remain the largest anatomic structure in the human body without known primary purpose. A hypothesis is that they are part of the adaptations that allow the brain to handle the volume and kinetic energy of each heartbeat. To test this hypothesis one needs a method to trace spatiotemporally the cardiac frequency phenomena of each single heartbeat of a sequence of heart beats.

Accordingly, this disclosure addresses the desire to reconstruct cardiac frequency angiographic phenomena with sufficient temporal resolution to isolate single vascular pulse waves, a capability not afforded by cardiac gated methods.

BRIEF DESCRIPTION OF THE INVENTION

The foregoing needs are met, to a great extent, by the disclosure, wherein in one aspect a technique and apparatus are provided for spatiotemporal reconstruction of a moving vascular pulse wave in the brain.

In accordance with one aspect, a method of extracting cardiac frequency phenomena from an angiographic study obtained at faster than cardiac frequency. When there is an instance of no significant motion alias, the method may include a wavelet transform of a pixel-wise time signals, filtering for cardiac wavelet scale, and inverse wavelet transformation. When there is an instance of significant motion alias, the method may include a high temporal resolution wavelet transform of a pixel-wise time signals, a high frequency wavelet transform of the overall angiographic intensity curve, a pixel-wise wavelet cross correlation of these, filtering for cardiac wavelet scale, and inverse wavelet transformation. When there is an instance of no significant motion alias, the method may include receiving angiographic data consisting of n by m pixels by q frames into computer memory; reformatting the angiographic data with a processor to generate an n by m array of time signals, each q samples long; applying a complex valued wavelet transform by the processor to each pixel-wise time signal to generate an n by m array of wavelet transforms; filtering the pixel-wise wavelet transforms for cardiac frequency by the processor; performing on the pixel-wise wavelet transforms data an inverse wavelet transform by the processor into time domain and reformatting into q frames of n by m pixels; and rendering each frame as an image with a brightness hue color model to represent a complex datum in each pixel with the processor. When there is an instance of significant motion alias, the method may include summing an angiographic signal for each time frame by a processor for all n by m pixels to generate an overall angiographic intensity point for each of q frames to generate an overall angiographic time intensity curve of length q; applying a high frequency resolution wavelet transform by the processor to the angiographic time intensity curve; reformatting then angiographic data by the processor as an n by m array of time signals each of length q; performing a high temporal wavelet transformation by the processor on each pixel-wise time signal to generate an n by m array of high temporal resolution wavelet transforms; cross correlating in wavelet domain, each pixel-wise high temporal resolution wavelet transform by a single high frequency resolution wavelet transform of an overall angiographic time intensity curve by the processor; inverse wavelet transforming an n by m array of cross-correlated signals in wavelet domain to generate an n by m array of time domain time signals each of length q by the processor; and reformatting the n by m time signals of length a by the processor into q frames of n by m pixels, each complex valued.

In accordance with one aspect, a device for extracting cardiac frequency phenomena from an angiographic study obtained at faster than cardiac frequency. The device in an instance of no significant motion alias may include a processor configured to receive angiographic data consisting of n by m pixels by q frames into a computer memory; the processor further configured to reformat the angiographic data to generate an n by m array of time signals, each q samples long; the processor further configured to apply a complex valued wavelet transform to each pixel-wise time signal to generate an n by m array of wavelet transforms; the processor further configured to filter the pixel-wise wavelet transforms for cardiac frequency; the processor further configured to perform on the pixel-wise wavelet transforms data an inverse wavelet transform into time domain and reformatting into q frames of n by m pixels; and the processor further configured to render each frame as an image with a brightness hue color model to represent a complex datum in each pixel. The device may include in an instance of significant motion alias, a processor configured to sum the angiographic signal for each time frame by the processor for all n by m pixels to generate an overall angiographic intensity point for each of the q frames to generate an overall angiographic time intensity curve of length q; the processor further configured to apply a high frequency resolution wavelet transform to the angiographic time intensity curve; the processor further configured to reformat then the angiographic data as an n by m array of time signals each of length q; the processor further configured to perform a high temporal wavelet transformation on each such pixel-wise time signal to generate an n by m array of high temporal resolution wavelet transforms; the processor further configured to cross correlate in wavelet domain, each pixel-wise high temporal resolution wavelet transform by the single high frequency resolution wavelet transform of an overall angiographic time intensity curve; the processor further configured to inverse wavelet transform the n by m array of cross-correlated signals in wavelet domain to generate an n by m array of time domain time signals each of length q; and the processor further configured to reformat the n by m time signals of length a into q frames of n by m pixels, each complex valued.

There has thus been outlined, rather broadly, certain aspects of the disclosure in order that the detailed description thereof herein may be better understood, and in order that the present contribution to the art may be better appreciated. There are, of course, additional aspects of the disclosure that will be described below and which will form the subject matter of the claims appended hereto.

According to the sampling theorem of Shannon, Nyqvist and Kotelnikov, to reconstruct a phenomenon such as a vascular pulse wave that transpires are cardiac frequency, one must sample at much higher than cardiac frequency. The method of this disclosure therefore requires raw data in the form of a brain angiogram acquired at much higher than cardiac frequency. The angiographic data sources where the method of this disclosure has been demonstrated and reduced to practice include ultrasound angiography, optical angiography, and a fluoroscopic angiography.

There are two requisites for reconstructing an individual vascular pulse wave (VPW). First, there must be experimental sampling at faster than cardiac frequency as governed by the sampling theorem of Nyqvist, Shannon, and Kotelnikov. Second, the reconstruction must conserve time-indexing since a VPW is time-variant. Unlike a Fourier transformed signal, a wavelet transformed signal retains time-indexing.

With ultrasound angiography, an ultrasound contrast agent, such as perflutren, is injected intravenously as a bolus, and ultrasound images are obtained of the brain at much higher than cardiac rate as the perflutren bolus travels through the brain. In one aspect, while ultrasound can image at a faster rate than cardiac rate, the blockage of sound by the skull bone impedes its sensitivity for this purpose. In a piglet cranial window model, ultrasound imaging is performed through a cranial window of a passing bolus of perflutren, an ultrasound contrast agent, in the dose of 1.2 million microspheres. The ultrasound video footage recorded at 30 Hz provides a cross-sectional angiogram of the brain. Other frequencies are contemplated as well.

With optical brain surface angiography, the brain surface is exposed, an intravenous dose of indocyanine green is injected, and images of the brain surface via an infrared pass optical filter are acquired at faster than cardiac frequency. In one aspect, the brain surface optical angiography is performed as a component of craniotomy for clipping of a brain artery aneurysm. After a clip has been applied to the neck of the aneurysm to exclude blood from entering it, a brain surface optical angiogram is obtained to confirm that blood does not enter the aneurysm and that the parent vessel of origin to the aneurysm has not been compromised by application of the clip. An operating microscope may be equipped with a beam splitter. One optical channel gives both wavelength views of the operative field. The other optical channel has a near infrared pass filter. At the moment of the optical angiogram, the anesthesiologist injects 25 mg of indocyanine green (ICG), a near infrared fluorescent agent. The field is stimulated with near infrared light and the fluorescence is captured as video footage at 30 Hz. Other frequencies are contemplated as well. This optical angiogram is obtained at significantly faster than cardiac rate.

With fluoroscopic angiography, an intravascular bolus of a water soluble iodinated contrast agent is injected as fluoroscopic x-ray images are obtained at much higher than cardiac frequency. In one aspect, humans with a suspected brain aneurysm, arteriovenous malformations, or cerebrovascular occlusive disease may undergo catheter cerebral angiography to confirm a diagnosis or as a part of the delivery of therapy. The fluoroscopic unit currently in clinical use for neuroangiography at Massachusetts General Hospital, the Siemens Artiz-Zee, records x-ray fluoroscopy images at up to 30 Hz, which is faster than cardiac rate. Other frequencies are contemplated as well. A dose of iodinated contrast is injected intravascularly and the angiographic footage is obtained during its passage across the vascular bed from the arterial to the venous component.

Given an angiogram obtained at faster than cardiac rate, the next step of this disclosure is to apply a wavelet filter to yield a time varying extraction of the cardiac frequency angiographic phenomena. There is prior art for the use of wavelets in the analysis of one-dimensional signals (U.S. Pat. No. 7,035,679B2) but not as images, and as noise correction tools in biomedical imaging (U.S. Pat. No. 7,602,183B2). But there is no prior art of wavelets for spatiotemporal reconstruction of cardiac frequency phenomena in images.

However, there may be cardiac-induced pulse motion of the organ including the vasculature undergoing the angiographic study, since the kinetic energy of the heart transmitted through blood vessels and blood may produce cardiac frequency to and fro movements of vessels containing angiographic contrast. The artifact with cardiac frequency wavelet filtering produced in this fashion is termed motion alias. This disclosure includes a method for attenuating motion alias by the use of high temporal wavelet resolution wavelet transforms. This method of attenuating motion alias is distinct from those methods that employ gating to compensate for example for respiratory motion (US patent publication number 2008/0226149A1).

The use of high temporal resolution wavelet transforms however may produce another artifact, frequency alias, where non-cardiac frequency phenomena pass through the high temporal resolution wavelet transform. This disclosure includes a method for the simultaneous attenuation of motion alias and frequency alias by the use of cross correlated high temporal and high frequency resolution wavelet transforms, each of different specific properties to be covered below.

In this respect, before explaining at least one aspect of the disclosure in detail, it is to be understood that the disclosure is not limited in its application to the details of construction and to the arrangements of the components set forth in the following description or illustrated in the drawings. The disclosure is capable of aspects in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the disclosure. It is important, therefore, that the claims be regarded as including such equivalent constructions insofar as they do not depart from the spirit and scope of the disclosure.

BRIEF DESCRIPTION OF THE DRAWINGS

The drawings illustrate preferred embodiments presently contemplated for carrying out the invention.

In the drawings.

DETAILED DESCRIPTION

Figure 1:
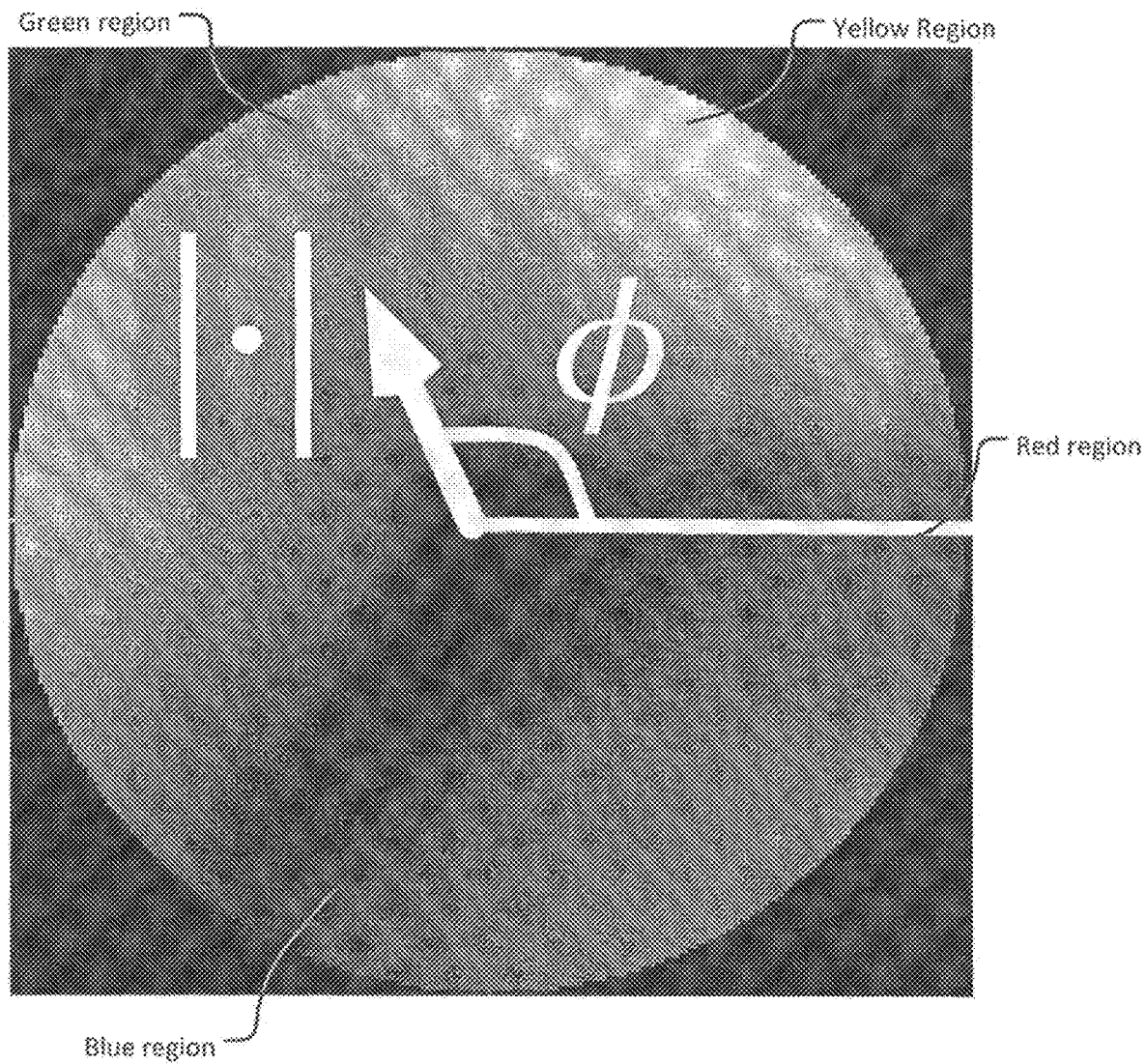
FIG. 1 illustrates a brightness hue color model for rendering a complex valued number according to aspects of the disclosure.

The disclosure will now be described with reference to the drawing figures, in which like reference numerals refer to like parts throughout. Aspects of the disclosure advantageously provide a method and device for spatiotemporal reconstruction of a moving vascular pulse wave in the brain.

The brain appears to have organized cardiac frequency angiographic phenomena with such coherence as to qualify as vascular pulse waves. Separate arterial and venous vascular pulse waves may be resolved. This disclosure states the method of extracting a spatiotemporal reconstruction of the cardiac frequency phenomena present in an angiogram obtained at faster than cardiac frequency. A wavelet transform is applied to each of the pixel-wise time signals of the angiogram. The cardiac frequency phenomena are extracted by setting to zero all wavelet coefficients except for those corresponding to cardiac wavelet scale. The result is inverse wavelet transformed pixel-wise to give a spatiotemporal grid of complex valued data representing cardiac frequency angiographic phenomena. If there is motion alias, which may be manifested by phase bimodality within the lumen of a vessel, then a modified method is applied. A high frequency resolution wavelet transform is applied to the overall angiographic time intensity curve. The pixel-wise time signals undergo each a high temporal resolution. Each of these pixel-wise high temporal resolution wavelet transforms is cross-correlated to the single high frequency resolution wavelet transform of the overall angiographic time intensity curve. The result is filtered for cardiac wavelet scale then pixel-wise inverse wavelet transformed. This gives a complex-valued spatiotemporal grid of cardiac frequency angiographic phenomena. It may be rendered with a brightness-hue color model or subjected to further analysis.

This disclosure is distinct from the common method of reconstructing cardiac frequency phenomenon by means of cardiac gating (United States patent publication numbers 2007/0106149A1 and US2007/0106146A1). In cardiac gating, a single cardiac cycle is interpolated from a large number of images acquired over the course of numerous cardiac cycle events. Cardiac gating is applied to methods that do not image at significantly faster than cardiac rate, for example magnetic resonance imaging (MRI) and computed tomography (CT). The method of cardiac gating does not allow the reconstruction of a single vascular pulse wave in a single cardiac cycle, as does this disclosure, nor the interactions between vascular pulse waves that are adjacent in time, as does this disclosure.

A ramification of the need to acquire several minutes of data per the method of cardiac gating is that it does not allow the separate imaging of vascular pulse waves attached to the arterial versus venous component of circulation. The method of this disclosure can reconstruct individual vascular pulse waves. By reconstructing them according to the delay in timing of the travel of an angiographic bolus, this method can reconstruct separate arterial and venous pulse waves, since the angiographic components of circulation are distinct in their time of flight, where the arterial component of an injected contrast bolus arrives sooner than the venous component.

One aspect of this disclosure is to extract cardiac frequency angiographic phenomena from an angiogram obtained at higher than cardiac frequency. A further aspect of this disclosure to do so even in the setting where there is motion alias due to pulse motion of the vessels containing the angiographic contrast.

A brain angiogram is obtained at higher than cardiac rate. An intravascular bolus of a contrast agent is injected and the passage of the bolus is imaged at faster than cardiac rate. Each image is termed a frame, and each frame consists of n by m pixels. This gives an angiographic data set of q frames of images with n by m pixels. The q frames are obtained with uniform time sampling, which may be measured in Hertz.

In the current aspect, each datum in an angiographic study is indexed by two spatial and one time index. This corresponds to a time-indexed sequence of two-dimensional images. The methods of this disclosure are not limited to two spatial dimensions and could be extended to three spatial dimensions with obvious modifications.

The preferred aspect uses complex valued data elements and complex valued wavelet transforms. However, similar results could be obtained with real valued data elements and real valued wavelet transforms.

This paragraph comments on the use of complex numbers in the current aspect of this disclosure. After the method of this disclosure has been applied to an angiogram to give a spatiotemporal representation of cardiac frequency angiographic phenomena, each complex number in spatiotemporal grid element represents the result of a wavelet cardiac frequency filter applied to an angiogram. A complex number may be represented in polar coordinates with a magnitude, since for a complex number $c=a+ib$ that represents a cardiac frequency angiographic phenomenon at a given space-time grid element, it has a polar representation $\{|c|, \phi d\}$ where the magnitude $|c|=\sqrt{a^2b^2}$ may be rendered as brightness and $\phi_c$, the angle between the positive x-axis and the point $\{a, b\}$, representing the phase of the cardiac frequency phenomenon at that space time element, as hue. The color model for rendering a complex valued number in a pixel is depicted in FIG. 1. In particular, FIG. 1 shows a spectrum of color hues with a green region, a yellow region, a red region, and a blue region noted (although the image is submitted as grayscale, one of ordinary skill in the art would recognize that this grayscale image includes a spectrum of hues). A sequence of such images may be animated across the time indices to represent a cine video sequence of the motions of a train of vascular pulse waves in the brain.

The steps of this disclosure after the import into computer memory of an angiogram depend on the presence or absence of motion alias. If there is no significant tissue motion then there is no motion alias. Then a reconstruction without accommodation for motion alias is applied, which is described as follows.

The angiographic data consisting of n by m pixels by q frames data is imported into computer memory and reformatted with the processor in memory to give an n by m array of time signals each q samples long.

A complex valued wavelet transform is applied by the processor to each pixel-wise time signal, giving an n by m array of wavelet transforms.

The pixel-wise wavelet transforms are filtered for cardiac frequency by the processor. This is done by setting to zero all wavelet coefficients that do not correspond to cardiac wavelet scale (in the field of wavelets this term corresponds to the concept of cardiac frequency).

The pixel-wise wavelet transforms data are inverse wavelet transformed by the processor into time domain and reformatted in computer memory into q frames of n by m pixels. Each data element (voxel) in this three dimensional grid is a complex valued number.

Each frame can be rendered as an image with a brightness hue color model to represent the complex datum in each pixel by the processor.

Cardiac frequency magnitude is represented as brightness and phase as hue.

The q images may be rendered as motion cine by the processor or they may be stored as a video file format such as Quicktime by the processor. The data may be analyzed in other ways including as running phase histograms.

If there is motion alias, then a modified algorithm is applied by the processor to the angiographic data after it has been imported into computer memory as follows:

The sum angiographic signal for each time frame is summed by the processor for all n by m pixels to give an overall angiographic intensity point. This is performed for each of the q frames to give an overall angiographic time intensity curve of length q.

A high frequency resolution wavelet transform is applied by the processor to this single angiographic time intensity curve.

Then the angiographic data is reformatted by the processor in computer memory as an n by m array of time signals each of length q.

A high temporal wavelet transformation is performed by the processor on each such pixel-wise time signal. This step yields an n by m array of high temporal resolution wavelet transforms.

In wavelet domain, each pixel-wise high temporal resolution wavelet transform is cross correlated (by simple multiplication) by the single high frequency resolution wavelet transform of the overall angiographic time intensity curve by the processor.

This n by m array of cross-correlated signals in wavelet domain is inverse wavelet transformed to give an n by m array of time domain time signals each of length q by the processor. Each datum in this n by m by q grid is complex valued.

The n by m time signals of length a are reformatted by the processor in computer memory into q frames of n by m pixels, each complex valued.

Each frame may be rendered as an image with a brightness hue color model by the processor, as above, or otherwise subjected to further analysis.

These wavelet methods of spatiotemporal reconstruction of angiographic cardiac frequency phenomena, both for data with and without motion alias, were generated by computational testing with simulated angiographic data and have been verified against biological optical, ultrasound, and fluoroscopic angiographic data. The methods for generating and testing against simulated angiographic data are not the topic of this disclosure.

The disclosure accordingly comprises the several steps and the relation of one or more of such steps with respect to each of the others, and the apparatus embodying features of construction, combinations of elements and arrangement of parts that are adapted to affect such steps, all is exemplified in the following detailed disclosure, and the scope of the disclosure will be indicated in the claims.

A notation is introduced to simplify the description of this disclosure. The lower case symbols $C_{i,j,t}$ are used to denote pixel-wise time signals, in which case the pixel indices i, j may be implied. The upper case symbol $$C_t = 1/nm * \Sigma_{i,j} C_{i,j,t}$$

is used to denote the frame-wise angiographic time intensity signal where i and j each range from 1 to the pixel dimensions respectively n and m. For $C_t$ the subscript t may be implied for brevity. For $C_{i,j,t}$ any or all of the subscripts i, j, t are implied if not explicitly given for brevity. The symbol $C_{i,j}$ denotes the angiographic time intensity curve across time corresponding to the i, $j^{th}$ pixel.

This disclosure employs a notation employing over symbols to specify the resolution characteristic of a wavelet transform. A wavelet transform of unspecified temporal and frequency resolution is denoted by the over bar symbol ‾, a high temporal resolution wavelet transform is denoted by the over hat symbol ^. A high frequency resolution wavelet transform is denoted with the over tilde symbol ~. Thus, for example, if the angiographic time intensity curve for the i, $j^{th}$ pixel is $C_{i,j}$, then its high temporal resolution wavelet transform is denoted by $\hat{C}_{i,j}$. For the overall angiographic time intensity curve C the high frequency resolution wavelet transform is denoted by $\tilde{C}$.

Figure 2:
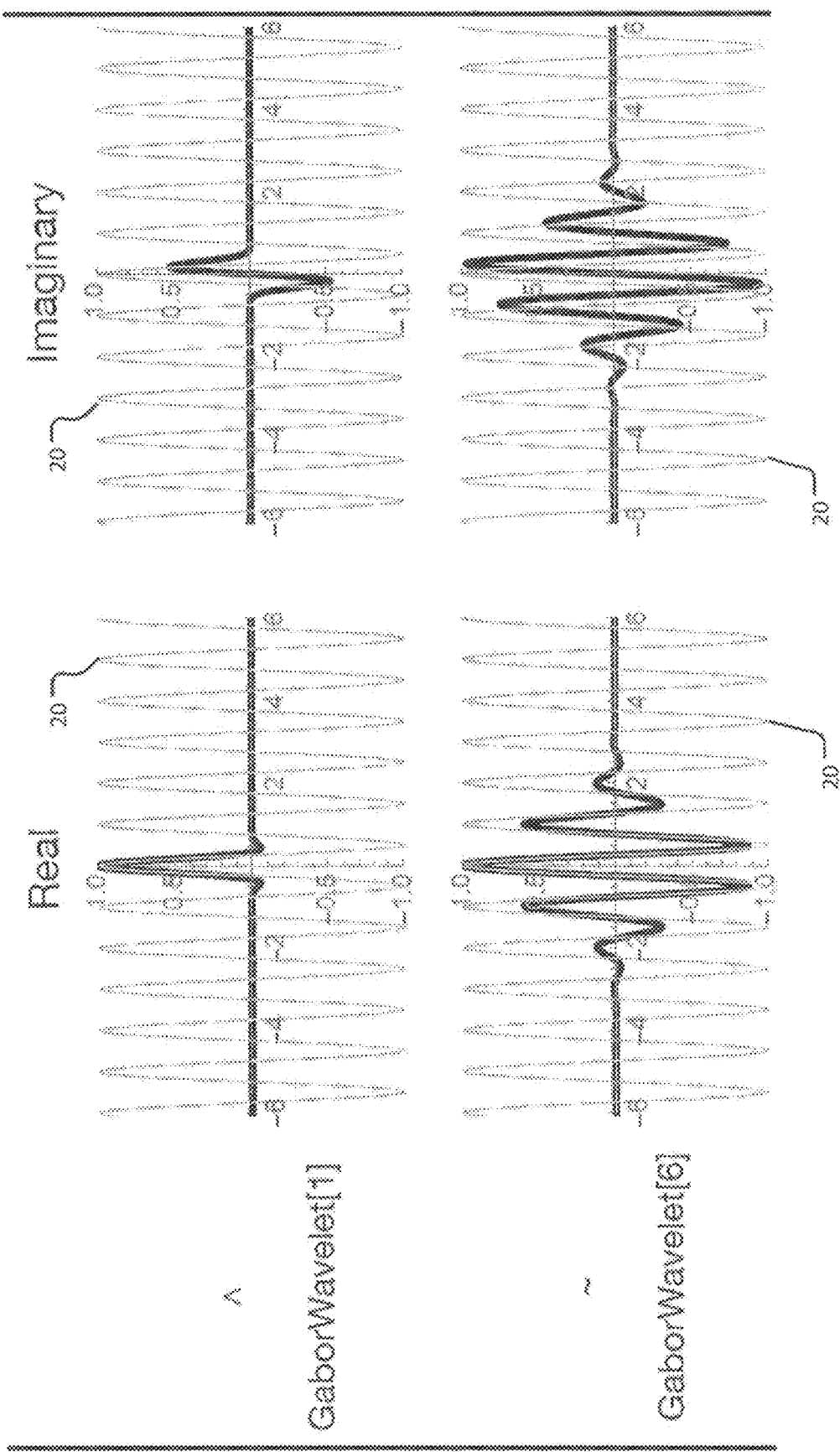
FIG. 2 illustrates a low and high temporal and frequency resolution wavelet Ψs, where the orange curves 20 are cardiac frequency sinusoids according to aspects of the disclosure.

In the current aspect, the computational code is written in the Wolfram language and is executed in the Mathematica version 10 environment (Wolfram Research, Urbana, Ill., USA). This environment provides the wavelet library employed by the current aspect. The Wolfram function GaborWavelet [1] is employed to compute a high temporal resolution wavelet transform and the function GaborWavelet [6] is employed to compute a high frequency resolution wavelet transform. The real and imaginary components of the wavelet Ψs employed by these functions are shown in FIG. 2.

Hereafter the detailed description of the current aspect is given with reference to the Wolfram language computer code that executes the steps of the disclosure. The Wolfram language favors the functional style of programming. The computer code is lightly edited for readability. Of course, other computational languages may be utilized as well.

In the current aspect, the raw angiographic data is supplied as a video file in the QuickTime format. It is imported into computer memory, changed from RGB color into grayscale by the processor, and each time-space grid element is changed into a floating point number ranging in [0., 1.] with the line:

angiographicFrames=Import["AngiographyVideoFileName.mov", "Data", "ColorSpace"→"Grayscale"][[All, All, All, 1]]/256

The frame-wise angiographic data is reformatted by the processor and stored in computer memory as a pixel-wise array of angiographic time signals corresponding to $C_{i,j}$ with the line:

angiographicTimeSignals=Transpose[angiographic-Frames, {3, 1, 2}]

Figure 3:
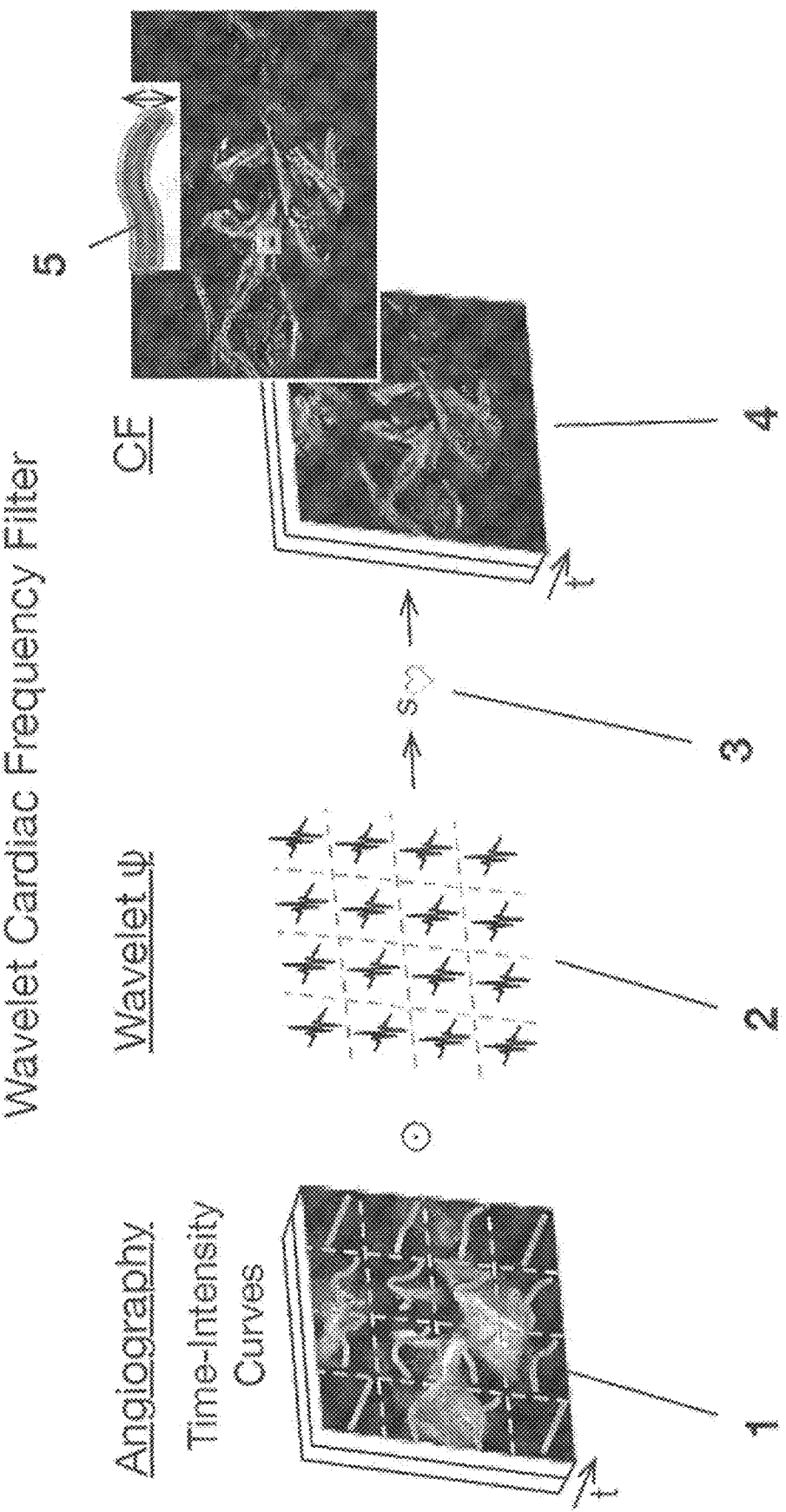
FIG. 3 illustrates wavelet spatiotemporal reconstruction of cardiac frequency angiographic phenomena according to aspects of the disclosure.

This step is illustrated by annotation [1] of FIG. 3.

The next step in the current aspect is the pixel-wise wavelet transforms and cardiac frequency filtering by extraction of the cardiac wavelet scale by the processor. These steps are illustrated respectively by annotations [2] and [3] of FIG. 3. The cardiac wavelet scale may be determined from the heart rate as obtained by any accepted physiological technique. The cardiac wavelet scale is closely related to the cardiac period (the reciprocal of the cardiac rate), and is represented in this computer code by the variable cardiacWaveletScale. The steps of pixel-wise wavelet transform, cardiac wavelet scale filtering, inverse wavelet transform, and data reformatting as video frames is performed by the processor by the line:

cardiacFrequencyAngiographicPhenomenaFrames=
Transpose[Map[InverseContinuousWaveletTransform [WaveletMapindexed[c→0c, ContinuousWaveletTransform [#, GaborWavelet[1]], Except[cardiacWaveletScale]]] &, angiographicTimeSignals, {2}], {2, 3, 1}]

This computer code variable cardiacFrequencyAngiographic-PhenomenaFrames contains the result after filtering for cardiac frequency angiographic phenomena. The pixel-wise inverse wavelet transforms and the frame-wise reformatting of the data are illustrated by annotation [4] of FIG. 3.

Since the original angiographic data are acquired at faster than cardiac frequency, the coherent spatiotemporal cardiac frequency phenomena present in it may represent single moving vascular pulse waves.

The detailed description of the method for the circumstance where there is significant motion alias follows. The presence of motion alias may be assessed from the presence of phase bimodality within the course of a single vessel. Motion alias is attenuated by the use of a high temporal resolution wavelet transform for the pixel-wise time signals. This injects frequency alias into the result. The frequency alias may be attenuated by the computation of "jointness" with a high frequency resolution wavelet transformation applied to a low noise physiological signal from the source. In the current aspect, the low noise signal is C. In the notation of this disclosure, the cardiac frequency angiographic phenomena with attenuated motion alias is calculated by the processor and stored in computer memory for the time signal at the $i, j^{th}$ pixel by the cross correlation of the pixel-wise high temporal resolution wavelet transforms by the high frequency resolution overall angiographic intensity curve $\tilde{C}$ as $$\hat{C}_{i,j}\overline{\tilde{C}} \quad (1)$$

Before proceeding with the pixel-wise high temporal resolution wavelet transforms, the overall angiographic time intensity curve denoted by is computed from the imported data with the line:

angiographicTimeIntensityCurve=Mean/@angiographic-Frames

Figure 4:
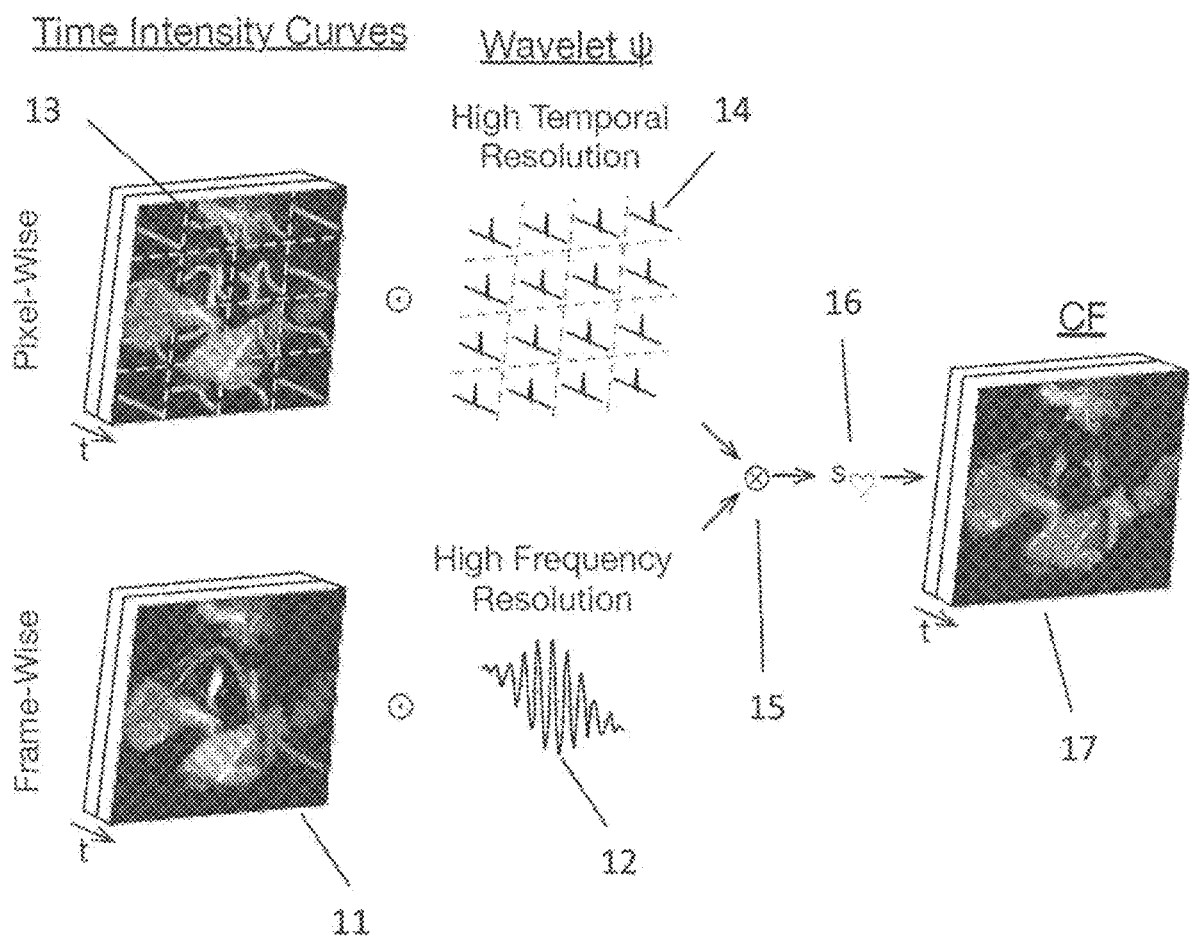
FIG. 4 illustrates wavelet spatiotemporal reconstruction of cardiac frequency angiographic phenomena where there is motion alias according to aspects of the disclosure.

This step is illustrated by annotation [11] of FIG. 4. Its high frequency resolution wavelet transform denoted to be used later is computed as:

tildeC=ContinuousWaveletTransform[angiographic-TimeIntensityCurve, GaborWavelet[6]]

This step is illustrated by annotation [12] of FIG. 4.

In the current aspect, the wavelet cross-correlation is computed by the processor by the function written in the Wolfram language:

waveletCrossCorrelation[w1_ContinuousWaveletData, w2_ContinuousWaveletData]:=Block[{xwd, normScale}, If[Not[w1['Wavelet']==w2['Wavelet'] && w1['Octaves']==w2['Octaves'] && w1['Voices']==w2['Voices']], Throw ['wavelet arguments do not match']]; xwd=Conjugate[w1[_, 'Values']]w2[_, 'Values']; ContinuousWaveletData[Thread [w1['WaveletIndex']→((*norm Scale*) xwd)], w1['Wavelet'], 'SampleRate'→w1['SampleRate']]]

With this function, the line that extracts cardiac frequency angiographic phenomena with attenuated motion alias based on $c_{i,j}\tilde{C}$ is:

cardiacFrequencyAngiographicPhenomenaFrames=
Transpose[Map[InverseContinuousWaveletTransform [WaveletMapindexed[c→0c, waveletCrossCorrelation[til-deC, ContinuousWaveletTransform[#, GaborWavelet[1]]], Except[cardiacOctaveVoice]]] &, channelArray, {2}], {2, 3, 1}]

The steps of this Wolfram language computer code are illustrated in FIG. 4 by annotation [14], the pixel-wise high temporal resolution wavelet transforms, annotation [15], the cross-correlation of the pixel-wise high temporal resolution wavelet transforms by the single high frequency resolution wavelet transform of the overall angiographic intensity curve, annotation [16], the filtering by cardiac wavelet scale, and annotation [17], the pixel-wise inverse wavelet transforms, reformatting of the data as frame-wise, and the rendering of complex-valued data using a brightness-hue color model.

An angiographic bolus travels first through the arterial and then through the venous components of circulation. The angiographic time of flight, reflected in the notation of this disclosure by the time index, t, may thus be used to separate arterial from venous angiographic phenomena from the data grid represented in computer memory by the variable cardiacFrequencyAngiographicPhenomenaFrames.

Figure 5:
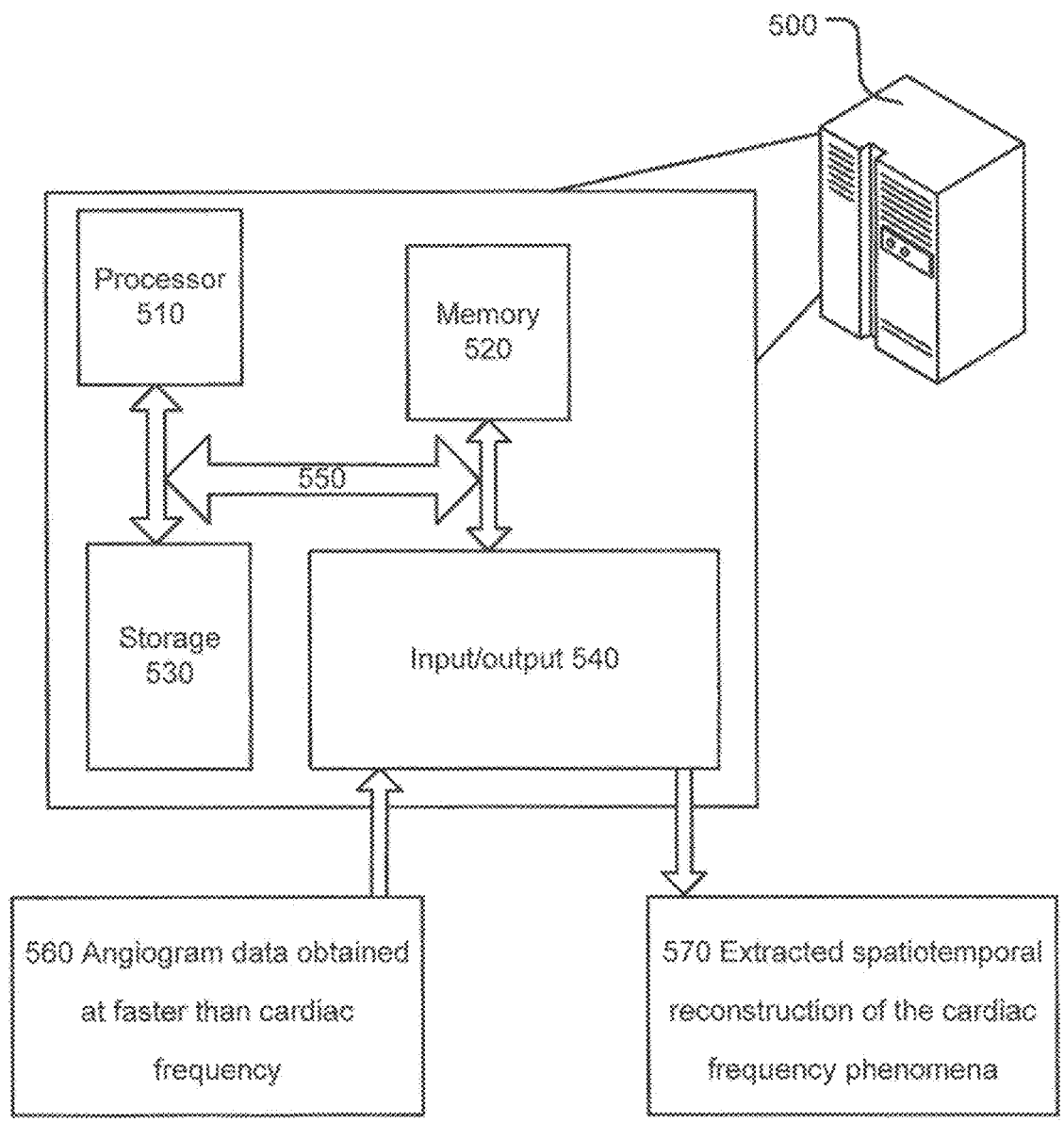
FIG. 5 shows a schematic diagram of an exemplary computer system for implementation of the disclosed process in accordance with aspects of the disclosure.

FIG. 5 shows a schematic diagram of an exemplary computer system in accordance with aspects of the disclosure. In particular, FIG. 5 illustrates a computer system 500 that can be used to implement the method to reconstruct the motions of vascular pulse waves in the brain. The computer system 500 includes a processor 510, a memory 520, a storage device 530, and an input/output device 540. Each of the components 510, 520, 530, and 540 can, for example, be interconnected using a system bus 550. The processor 510 is capable of processing instructions for execution of the method to reconstruct the motions of vascular pulse waves in the brain within the computer system 500. In one aspect, the processor 510 is a non-generic medical imaging processor. In one implementation, the processor 510 is a single-threaded processor. In another implementation, the processor 510 is a multi-threaded processor. The processor 510 is capable of processing instructions stored in the memory 520 or on the storage device 530 to reconstruct the motions of vascular pulse waves in the brain. In some aspects, a parallel processing set of computer systems 500 connected over a network may be employed, clustered into one or more server centers.

The input/output 540 may output the reconstructed motions of vascular pulse waves in the brain on a display, a printer, or the like. In one aspect, the input/output 540 may receive angiogram data obtained at faster than cardiac frequency 560. The angiogram data obtained at faster than cardiac frequency 560 may be processed by the processor 510 as noted above. The processor 510 producing extracted spatiotemporal reconstruction of the cardiac frequency phenomena 570. In one aspect, the input/output 540 may output the extracted spatiotemporal reconstruction of the cardiac frequency phenomena 570.

The memory 520 stores information within the computer system 500. In one implementation, the memory 520 is a computer-readable medium. In one implementation, the memory 520 is a volatile memory unit. In another implementation, the memory 520 is a non-volatile memory unit. The storage device 530 is capable of providing mass storage for the computer system 500. In one implementation, the storage device 530 is a computer-readable medium. In various different implementations, the storage device 530 can, for example, include a hard disk device, an optical disk device, or some other large capacity storage device. The input/output device 540 provides input/output operations for the computer system 500.

The resulting determined cardiac frequency angiographic phenomenon is used for comparison to target values to diagnose certain disorders. Moreover, the resulting determined cardiac frequency angiographic phenomenon is used for comparison to previous values to determine whether a particular medical treatment is beneficial, or the like. In this regard, it is believed that the ventricles of the brain, the largest anatomic structure without known primary function, serve to accommodate the passage of vascular pulse waves in the brain. Hydrocephalus, a disorder of the brain ventricles, affects about 1 in 500 live births but can occur at any age. The management of it is unsatisfactory and has not improved in decades. The disclosure will enhance the advancement of hydrocephalus management by determining why the brain has ventricles. Relatedly, intracranial pressure has a waveform but no one knows its basis. The disclosed method to image brain vascular pulse waves will help determine the basis of the intracranial pressure waveform. About 100,000 intracranial pressure monitoring systems are implanted in the USA per year for head trauma. These devices all capture a waveform of unknown significance.

The disclosure may be implemented in any type of computing devices, such as, e.g., a desktop computer, personal computer, a laptop/mobile computer, a personal data assistant (PDA), a mobile phone, a tablet computer, cloud computing device, and the like, with wired/wireless communications capabilities via the communication channels.

Further in accordance with various aspects of the disclosure, the methods described herein are intended for operation with dedicated hardware implementations including, but not limited to, PCs, PDAs, semiconductors, application specific integrated circuits (ASIC), programmable logic arrays, cloud computing devices, and other hardware devices constructed to implement the methods described herein.

It should also be noted that the software implementations of the disclosure as described herein are optionally stored on a tangible storage medium, such as: a magnetic medium such as a disk or tape; a magneto-optical or optical medium such as a disk; or a solid state medium such as a memory card or other package that houses one or more read-only (non-volatile) memories, random access memories, or other re-writable (volatile) memories. A digital file attachment to email or other self-contained information archive or set of archives is considered a distribution medium equivalent to a tangible storage medium. Accordingly, the disclosure is considered to include a tangible storage medium or distribution medium, as listed herein and including art-recognized equivalents and successor media, in which the software implementations herein are stored.

Additionally, the various aspects of the disclosure may be implemented in a non-generic computer implementation. Moreover, the various aspects of the disclosure set forth herein improve the functioning of the system as is apparent from the disclosure hereof. Furthermore, the various aspects of the disclosure involve computer hardware that it specifically programmed to solve the complex problem addressed by the disclosure. Accordingly, the various aspects of the disclosure improve the functioning of the system overall in its specific implementation to perform the process set forth by the disclosure and as defined by the claims.

The many features and advantages of the disclosure are apparent from the detailed specification, and, thus, it is intended by the appended claims to cover all such features and advantages of the disclosure which fall within the true spirit and scope of the disclosure. Further, since numerous modifications and variations will readily occur to those skilled in the art, it is not desired to limit the disclosure to the exact construction and operation illustrated and described, and, accordingly, all suitable modifications and equivalents may be resorted to that fall within the scope of the disclosure.

What is claimed is:

1. A system for extracting cardiac frequency angiographic phenomena from an angiographic study, the system comprising:
a processor programmed to:
receive angiographic data from an angiographic study obtained at a rate faster than cardiac frequency;
apply a mathematical transform analysis that conserves time-indexing to the angiographic data to yield a spatiotemporal representation of cardiac frequency angiographic phenomena; and
generate images of the cardiac frequency angiographic phenomena from the spatiotemporal representation of the cardiac frequency angiographic phenomena.

2. The system of claim 1 wherein, in applying the mathematical transform analysis that conserves time-indexing, the processor is further programmed to:
detect a motion alias resulting from pulse motion of vessels in an organ on which the angiographic study was performed;
apply a first mathematical transform analysis that conserves time-indexing to the angiographic data if a motion alias is not detected; and
apply a second mathematical transform analysis that conserves time-indexing to the angiographic data if a motion alias is detected.

3. The system of claim 2 wherein, in applying the first mathematical transform analysis that conserves time-indexing, the processor is programmed to:
reformat the angiographic data from q frames of n by m pixels to an n by m array of time signals, each q samples long;
apply a complex valued wavelet transform to each pixel-wise time signal to generate an n by m array of wavelet transforms;
filter the pixel-wise wavelet transforms for cardiac frequency;
perform on the pixel-wise wavelet transforms an inverse wavelet transform into time domain;
reformat the pixel-wise inverse wavelet transforms into q frames of n by m pixels; and
render each frame as an image with a brightness-hue color model to represent a complex datum in each pixel.

4. The system of claim 2 wherein, in applying the second mathematical transform analysis that conserves time-indexing, the processor is programmed to:
sum an angiographic signal from the angiographic data for each of q frames of n by m pixels, to generate an overall angiographic intensity point for each of q frames to generate an overall angiographic time intensity curve of length q;
apply a high frequency resolution wavelet transform to the angiographic time intensity curve;
reformat the angiographic data as an n by m array of time signals each of length q;
perform a high temporal wavelet transformation on each pixel-wise time signal to generate an n by m array of high temporal resolution wavelet transforms;
cross-correlate, in a wavelet domain, each pixel-wise high temporal resolution wavelet transform by a single high frequency resolution wavelet transform of the overall angiographic time intensity curve;
inverse wavelet transform an n by m array of cross-correlated signals in the wavelet domain to generate an n by m array of time domain time signals each of length q;
reformat the n by m time signals of length q into q frames of n by m pixels, each complex valued; and
render each frame as an image with a brightness-hue color model to represent a complex datum in each pixel.

5. The system of claim 4 wherein application of the second wavelet transform analysis provides for attenuation of the motion alias, as well as attenuation of a frequency alias.

6. The system of claim 1 wherein the cardiac frequency angiographic phenomena comprises vascular pulse waves in an organ on which the angiographic study was performed; and wherein, in generating images of the cardiac frequency angiographic phenomena, the processor is programmed to generate a sequence of images that display motions of a train of vascular pulse waves in the organ.

7. The system of claim 1 wherein the angiographic study from which the angiographic data is obtained comprises one of ultrasound angiography, optical angiography, and fluoroscopic angiography.

8. A computer-implemented method for extracting cardiac frequency angiographic phenomena from an angiographic study obtained at a rate faster than cardiac frequency, the method comprising:
receiving angiographic data from an angiographic study obtained at a rate faster than cardiac frequency; and
applying a mathematical transform analysis that conserves time-indexing to the angiographic data to output a spatiotemporal reconstruction of cardiac frequency angiographic phenomena displayed in one or more images.

9. The computer-implemented method of claim 8 wherein applying the mathematical transform analysis that conserves time-indexing further comprises:
detecting a motion alias resulting from pulse motion of vessels in an organ on which the angiographic study was performed;
applying a first wavelet transform analysis to the angiographic data if a motion alias is not detected; and
applying a second wavelet transform analysis to the angiographic data if a motion alias is detected.

10. The computer-implemented method of claim 9 wherein applying the first wavelet transform analysis further comprises:
reformatting the angiographic data from q frames of n by m pixels to an n by m array of time signals, each q samples long;
applying a complex valued wavelet transform to each pixel-wise time signal to generate an n by m array of wavelet transforms;
filtering the pixel-wise wavelet transforms for cardiac frequency;
performing on the pixel-wise wavelet transforms an inverse wavelet transform into time domain;
reformatting the pixel-wise inverse wavelet transforms into q frames of n by m pixels; and
rendering each frame as an image with a brightness-hue color model to represent a complex datum in each pixel.

11. The computer-implemented method of claim 9 wherein applying the second wavelet transform analysis further comprises:
summing an angiographic signal from the angiographic data for each of q frames of n by m pixels, to generate an overall angiographic intensity point for each of q frames to generate an overall angiographic time intensity curve of length q;
applying a high frequency resolution wavelet transform to the angiographic time intensity curve;
reformatting the angiographic data as an n by m array of time signals each of length q;
performing a high temporal wavelet transformation on each pixel-wise time signal to generate an n by m array of high temporal resolution wavelet transforms;
cross-correlating, in a wavelet domain, each pixel-wise high temporal resolution wavelet transform by a single high frequency resolution wavelet transform of the overall angiographic time intensity curve;
inverse wavelet transforming an n by m array of cross-correlated signals in the wavelet domain to generate an n by m array of time domain time signals each of length q;
reformatting the n by m time signals of length q into q frames of n by m pixels, each complex valued; and
rendering each frame as an image with a brightness-hue color model to represent a complex datum in each pixel.

12. The computer-implemented method of claim 8 wherein the cardiac frequency angiographic phenomena comprises vascular pulse waves in an organ on which the angiographic study was performed; and
wherein outputting the spatiotemporal reconstruction of cardiac frequency angiographic phenomena displayed in one or more images further comprises displaying motions of the vascular pulse waves in the organ.

13. A system for extracting cardiac frequency phenomena from an angiographic study of an organ, the system comprising:
a processor programmed to:
receive angiographic data obtained at a rate faster than cardiac frequency;
determine a presence of a motion alias resulting from pulse motion of vessels in the organ;
when motion alias is determined to be present, perform a first mathematical transform analysis that conserves time-indexing on the angiographic data to extract a spatiotemporal reconstruction of the cardiac frequency phenomena; and
when no motion alias is determined to be present, perform a second mathematical transform analysis that conserves time-indexing on the angiographic data to extract a spatiotemporal reconstruction of the cardiac frequency phenomena.

14. The system of claim 13 wherein, in applying the second mathematical transform analysis that conserves time-indexing, the processor is programmed to:
   reformat the angiographic data from q frames of n by m pixels to an n by m array of time signals, each q samples long;
   apply a complex valued wavelet transform to each pixel-wise time signal to generate an n by m array of wavelet transforms;
   filter the pixel-wise wavelet transforms for cardiac frequency;
   perform on the pixel-wise wavelet transforms an inverse wavelet transform into time domain;
   reformat the pixel-wise inverse wavelet transforms into q frames of n by m pixels; and
   render each frame as an image with a brightness-hue color model to represent a complex datum in each pixel.

15. The system of claim 13 wherein, in applying the second mathematical transform analysis that conserves time-indexing, the processor is programmed to:
   sum an angiographic signal from the angiographic data for each of q frames of n by m pixels, to generate an overall angiographic intensity point for each of q frames to generate an overall angiographic time intensity curve of length q;
   apply a high frequency resolution wavelet transform to the angiographic time intensity curve;
   reformat the angiographic data as an n by m array of time signals each of length q;
   perform a high temporal wavelet transformation on each pixel-wise time signal to generate an n by m array of high temporal resolution wavelet transforms;
   cross-correlate, in a wavelet domain, each pixel-wise high temporal resolution wavelet transform by a single high frequency resolution wavelet transform of the overall angiographic time intensity curve;
   inverse wavelet transform an n by m array of cross-correlated signals in the wavelet domain to generate an n by m array of time domain time signals each of length q;
   reformat the n by m time signals of length q into q frames of n by m pixels, each complex valued; and
   render each frame as an image with a brightness-hue color model to represent a complex datum in each pixel.

* * * * *